(12) United States Patent
Fairman

(10) Patent No.: US 10,835,590 B2
(45) Date of Patent: Nov. 17, 2020

(54) PERIODONTITIS VACCINE AND RELATED COMPOSITIONS AND METHODS OF USE

(71) Applicant: Vaxcyte, Inc., Foster City, CA (US)

(72) Inventor: Jeffery Fairman, Mountain View, CA (US)

(73) Assignee: Vaxcyte, Inc., Foster City, CA (US)

( * ) Notice: Subject to any disclaimer, the term of this patent is extended or adjusted under 35 U.S.C. 154(b) by 0 days.

(21) Appl. No.: 16/158,155

(22) Filed: Oct. 11, 2018

(65) Prior Publication Data

US 2019/0192645 A1 Jun. 27, 2019

Related U.S. Application Data

(60) Provisional application No. 62/571,582, filed on Oct. 12, 2017.

(51) Int. Cl.
| | | |
|---|---|---|
| *C07K 1/00* | (2006.01) | |
| *A61K 39/02* | (2006.01) | |
| *A61K 39/00* | (2006.01) | |

(52) U.S. Cl.
CPC ...... *A61K 39/0216* (2013.01); *A61K 2039/54* (2013.01); *A61K 2039/542* (2013.01); *A61K 2039/543* (2013.01); *A61K 2039/55505* (2013.01); *A61K 2039/55572* (2013.01); *A61K 2039/70* (2013.01)

(58) Field of Classification Search
CPC .................................................. A61K 39/0216
See application file for complete search history.

(56) References Cited

FOREIGN PATENT DOCUMENTS

| | | |
|---|---|---|
| WO | 1997016542 A1 | 5/1997 |
| WO | 1997034629 A1 | 9/1997 |
| WO | 2000072875 A1 | 12/2000 |
| WO | 2001047961 A1 | 7/2001 |
| WO | 2005112993 A1 | 12/2005 |
| WO | 2011097688 A1 | 8/2011 |
| WO | 2017066719 A2 | 4/2017 |

OTHER PUBLICATIONS

"PCT Search Report and Written Opinion, PCT/US2018/055496", dated Feb. 18, 2019.

Bai, Donying, et al., "Immunoreactive antigens recognized in serum samples from mice intranasally immunized with Porphyromonas gingivalis outer membrane vesicles", Pathogens and Disease, vol. 73, No. 3, Dec. 4, 2014.

Frazer, L. T., et al., "Vaccination with recombinant adhesins from the RgpA-Kgp proteinase-adhesin complex protects against Porphyromonas gingivalis infection", Vaccine, Elsevier, Amsterdam, NL, vol. 24, No. 42-43, Oct. 30, 2006, pp. 6542-6554.

Gibson III, Frank C., et al., "Prevention of Porphyromonas gingivalis-induced oral bone loss following immunization with gingipain R1", Infection and Immunity, American Society for Microbiology, US, vol. 69, No. 12, Dec. 1, 2001, pp. 7959-7963.

Li, N. , et al., "Gingipains from Porphyromonas gingivalis—complex domain structures confer diverse functions", European Journal of Microbiology and Immunology, vol. 1, No. 1, Mar. 1, 2011, pp. 41-58.

Nakao, Ryoma , et al., "Outer Membrane Vesicles of Porphyromonas gingivalis Elicit a Mucosal Immune Response", PLOS ONE, vol. 6, No. 10, Oct. 14, 2011, p. e26163.

Ryoma, Nakao , et al., "Assessment of outer membrane vesicles of peridontopathic bacterium Porphyromonas gingivalisas possible mucosal immuogen", Vaccine, Elsevier, Amsterdam, NL, vol. 34, No. 28, Jul. 25, 2016, p. 4628.

Vieth, Paul D., et al., "Porphyromonas gingivalis Outer Membrane Vesicles Exclusively Contain Outer Membrane and Periplasmic Proteins and Carry a Cargo Enriched with Virulence Factors", Journal of Proteome Research, vol. 3, No. 5, Apr. 5, 2014, pp. 2420-2432.

Huang, N. et al. (2018). "Immunization with cell-free-generated vaccine protects from *porphyromonas gingivalis*-induced alveolar bone loss," J. Clin. Periodontol. 46:197-205.

*Primary Examiner* — Albert M Navarro
(74) *Attorney, Agent, or Firm* — Cooley LLP

(57) ABSTRACT

An immunogenic composition, a periodontal vaccine formulation containing the immunogenic composition, and methods for treating or preventing periodontal disease are provided, where the methods involves administering an immunologically effective amount of the composition or vaccine formulation to a subject. The immunogenic composition contains at least one polypeptide that comprises: an Mfa1 antigen sequence that is substantially homologous to an immunogenic amino acid sequence from an Mfa1 fimbrilin protein of a *Porphyromonas* bacterium; and an HA1 antigen sequence, an HA2 antigen sequence, or both an HA1 antigen sequence and an HA2 antigen sequence, wherein the HA1 antigen sequence is substantially homologous to an immunogenic amino acid sequence from an RgpA Gingipain hemagglutinin domain 1 contained within an RgpA Gingipain protein of a *Porphyromonas* bacterium, and the HA2 antigen sequence is substantially homologous to an immunogenic amino acid sequence from an RgpA Gingipain hemagglutinin domain 2 contained within an RgpA Gingipain protein of a *Porphyromonas* bacterium.

43 Claims, 3 Drawing Sheets

Specification includes a Sequence Listing.

```
                        SEQUENCE LISTING

<160> NUMBER OF SEQ ID NOS: 6

<210> SEQ ID NO 1
<211> LENGTH: 543
<212> TYPE: PRT
<213> ORGANISM: Porphyromonas gingivalis
<223> OTHER INFORMATION: Mfa1 fimbrilin

<400> SEQUENCE: 1

Met Gly Asn Gly Pro Asp Pro Asp Asn Ala Ala Lys Ser Tyr Met Ser
1               5                   10                  15

Met Thr Leu Ser Met Pro Met Gly Ser Ala Arg Asp Gly Gln Asn Gln
            20                  25                  30

Asp Asn Pro Gln Tyr Asn Phe Val Gly Glu Trp Ala Gly Lys Asp Lys
        35                  40                  45

Ile Glu Lys Val Ser Ile Tyr Met Val Pro Gln Gly Gly Pro Gly Leu
    50                  55                  60

Val Glu Ser Ala Glu Asp Leu Asp Phe Gly Thr Tyr Tyr Asp Ala Pro
65                  70                  75                  80

Thr Gln Glu Ala Gly Ser Asn Asn Val Ile Leu Lys Pro Lys Lys Gly
                85                  90                  95

Ile Lys Val Asn Ser Ala Val Gly Lys Thr Val Lys Val Tyr Val Val
            100                 105                 110

Leu Asn Asp Ile Ala Gly Lys Ala Lys Ala Leu Leu Ala Asn Val Asn
        115                 120                 125

Ala Val Asp Phe Glu Ala Lys Phe Lys Glu Val Ile Glu Leu Ser Thr
    130                 135                 140

Gln Ala Gln Ala Leu Gly Thr Val Ala Asp Gly Pro Asn Pro Ala Thr
145                 150                 155                 160

Ala Ala Gly Lys Ile Ala Lys Lys Asn Gly Val Asp Asn Glu Thr Ile
                165                 170                 175

Met Met Thr Cys Phe Glu Pro Ser Ala Pro Leu Thr Ile Glu Ala Ala
            180                 185                 190

Val Ser Glu Ala Asn Ala Ile Ala Gly Val Lys Asn Gln Ala Lys Val
        195                 200                 205

Thr Val Glu Arg Ser Val Ala Arg Ala Met Val Ser Thr Lys Ala Glu
    210                 215                 220

Ser Tyr Glu Ile Lys Ala Thr Thr Gln Ile Gly Ser Ile Ala Ala Gly
225                 230                 235                 240

Asp Val Leu Ala Thr Val Ser Asp Ile Arg Trp Val Val Ala Gln Gly
                245                 250                 255

Glu Arg Lys Gln Tyr Leu Ser Lys Lys Arg Gly Thr Val Pro Glu Asn
            260                 265                 270

Thr Trp Val Thr Pro Gly Ser Asp Tyr Ile Ser Thr Asn Ala Asn Phe
        275                 280                 285

His Ala Gln Ala Thr Met Tyr Tyr Asp Tyr Thr Gly Leu Trp Asp Asp
    290                 295                 300

His Asn Ala Asp Pro Thr Met Val Ser Gly Thr Lys Val Pro Thr Leu
305                 310                 315                 320

Ala Asn Tyr Gln Leu Gln Asp Val Thr Asp Glu Leu Ala Gln Arg Leu
                325                 330                 335
```

```
Ser Gly Lys Phe Leu Pro Asn Thr His Lys Ser Gly Ile Asp Ala
            340                 345                 350

Ala Thr Ser His Tyr Lys Arg Gly Asn Thr Ala Tyr Val Leu Val Arg
            355                 360                 365

Ala Lys Phe Thr Pro Lys Lys Glu Ala Phe Ile Asp Lys Gly Lys Asp
            370                 375                 380

Tyr Thr Asp Gly Thr Pro Val Pro Glu Tyr Thr Asp Gly Asp Asp Phe
385                 390                 395                 400

Phe Val Gly Glu Asn Gly Gln Phe Tyr Val Ser Met Lys Ser Val Thr
                405                 410                 415

Asp Pro Lys Val Gly Val Ala Gly Met Lys Ala His Lys Tyr Val
            420                 425                 430

Lys Gly Lys Val Leu Tyr Tyr Ala Trp Leu Asn Pro Ser Thr Thr Ser
            435                 440                 445

Pro Asp Ser Trp Trp Asn Ser Pro Val Val Arg Asn Asn Ile Tyr His
            450                 455                 460

Ile His Ile Lys Ser Ile Lys Lys Leu Gly Phe Asn Trp Asn Pro Leu
465                 470                 475                 480

Val Pro Asn Pro Gln Asn Pro Asn Asp Pro Asn Gly Pro Ile Asn Pro
            485                 490                 495

Asn Asn Pro Asp Pro Asn Pro Asp Glu Pro Gly Thr Pro Ile Pro Thr
            500                 505                 510

Asp Pro Glu Gln Pro Leu Pro Asp Gln Asp Thr Phe Met Ser Val Glu
            515                 520                 525

Val Thr Val Leu Pro Trp Lys Val His Ser Tyr Glu Val Asp Leu
            530                 535                 540

<210> SEQ ID NO 2
<211> LENGTH: 167
<212> TYPE: PRT
<213> ORGANISM: Porphyromonas gingivalis
<223> OTHER INFORMATION: Gingipain HA1

<400> SEQUENCE: 2

Met Leu Ser Glu Ser Phe Glu Asn Gly Ile Pro Ala Ser Trp Lys Thr
1               5                   10                  15

Ile Asp Ala Asp Gly Asp Gly His Gly Trp Lys Pro Gly Asn Ala Pro
            20                  25                  30

Gly Ile Ala Gly Tyr Asn Ser Asn Gly Cys Val Tyr Ser Glu Ser Phe
            35                  40                  45

Gly Leu Gly Gly Ile Gly Val Leu Thr Pro Asp Asn Tyr Leu Ile Thr
        50                  55                  60

Pro Ala Leu Asp Leu Pro Asn Gly Gly Lys Leu Thr Phe Trp Val Cys
65                  70                  75                  80

Ala Gln Asp Ala Asn Tyr Ala Ser Glu His Tyr Ala Val Tyr Ala Ser
                85                  90                  95

Ser Thr Gly Asn Asp Ala Ser Asn Phe Thr Asn Ala Leu Leu Glu Glu
            100                 105                 110

Thr Ile Thr Ala Lys Gly Val Arg Ser Pro Glu Ala Ile Arg Gly Arg
            115                 120                 125

Ile Gln Gly Thr Trp Arg Gln Lys Thr Val Asp Leu Pro Ala Gly Thr
        130                 135                 140

Lys Tyr Val Ala Phe Arg His Phe Gln Ser Thr Asp Met Phe Tyr Ile
145                 150                 155                 160
```

Asp Leu Asp Glu Val Glu Ile
            165

<210> SEQ ID NO 3
<211> LENGTH: 433
<212> TYPE: PRT
<213> ORGANISM: Porphyromonas gingivalis
<223> OTHER INFORMATION: Gingipain HA2

<400> SEQUENCE: 3

Met Phe Thr Glu Thr Phe Glu Ser Ser Thr His Gly Glu Ala Pro Ala
1               5                   10                  15

Glu Trp Thr Thr Ile Asp Ala Asp Gly Asp Gln Asp Trp Leu Cys
            20                  25                  30

Leu Ser Ser Gly Gln Leu Asp Trp Leu Thr Ala His Gly Gly Thr Asn
            35                  40                  45

Val Val Ala Ser Phe Ser Trp Asn Gly Met Ala Leu Asn Pro Asp Asn
        50                  55                  60

Tyr Leu Ile Ser Lys Asp Val Thr Gly Ala Thr Lys Val Lys Tyr Tyr
65                  70                  75                  80

Tyr Ala Val Asn Asp Gly Phe Pro Gly Asp His Tyr Ala Val Met Ile
                85                  90                  95

Ser Lys Thr Gly Thr Asn Ala Gly Asp Phe Thr Val Val Phe Glu Glu
            100                 105                 110

Thr Pro Asn Gly Ile Asn Lys Gly Gly Ala Arg Phe Gly Leu Ser Thr
            115                 120                 125

Glu Ala Asn Gly Ala Lys Pro Gln Ser Val Trp Ile Glu Arg Thr Val
130                 135                 140

Asp Leu Pro Ala Gly Thr Lys Tyr Val Ala Phe Arg His His Asn Cys
145                 150                 155                 160

Ser Asp Leu Asn Tyr Ile Leu Leu Asp Asp Ile Gln Phe Thr Met Gly
                165                 170                 175

Gly Ser Pro Thr Pro Thr Asp Tyr Thr Tyr Thr Val Tyr Arg Asp Gly
            180                 185                 190

Thr Lys Ile Lys Glu Gly Leu Thr Glu Thr Thr Phe Glu Glu Asp Gly
            195                 200                 205

Val Ala Thr Gly Asn His Glu Tyr Cys Val Glu Val Lys Tyr Thr Ala
        210                 215                 220

Gly Val Ser Pro Lys Val Cys Val Asn Val Thr Ile Asn Pro Thr Gln
225                 230                 235                 240

Phe Asn Pro Val Lys Asn Leu Lys Ala Gln Pro Asp Gly Gly Asp Val
                245                 250                 255

Val Leu Lys Trp Glu Ala Pro Ser Gly Lys Arg Gly Glu Leu Leu Asn
            260                 265                 270

Glu Asp Phe Glu Gly Asp Ala Ile Pro Thr Gly Trp Thr Ala Leu Asp
            275                 280                 285

Ala Asp Gly Asp Gly Asn Asn Trp Asp Ile Thr Leu Asn Glu Phe Thr
        290                 295                 300

Arg Gly Glu Arg His Val Leu Ser Pro Leu Arg Ala Ser Asn Val Ala
305                 310                 315                 320

Ile Ser Tyr Ser Ser Leu Leu Gln Gly Gln Glu Tyr Leu Pro Leu Thr
                325                 330                 335

Pro Asn Asn Phe Leu Ile Thr Pro Lys Val Glu Gly Ala Lys Lys Ile
            340                 345                 350

Thr Tyr Lys Val Gly Ser Pro Gly Leu Pro Gln Trp Ser His Asp His

```
                    355                 360                 365
Tyr Ala Leu Cys Ile Ser Lys Ser Gly Thr Ala Ala Asp Phe Glu
            370                 375                 380
Val Ile Phe Glu Glu Thr Met Thr Tyr Thr Gln Gly Gly Ala Asn Leu
385                 390                 395                 400
Thr Arg Glu Lys Asp Leu Pro Ala Gly Thr Lys Tyr Val Ala Phe Arg
                405                 410                 415
His Tyr Asn Cys Thr Asp Val Leu Gly Ile Met Ile Asp Val Val
            420                 425                 430
Ile
```

<210> SEQ ID NO 4
<211> LENGTH: 539
<212> TYPE: PRT
<213> ORGANISM: Porphyromonas gulae
<223> OTHER INFORMATION: Mfa fimbrilin

<400> SEQUENCE: 4

```
Met Gly Asn Gly Pro Asp Pro Asp Asn Ala Ala Lys Ser Tyr Met Ser
1               5                   10                  15
Met Thr Leu Ser Met Pro Leu Gly Ser Ala Arg Ala Gly Asp Gly Gln
            20                  25                  30
Asp Gln Pro Asn Pro Asp Tyr Asn Tyr Val Gly Glu Trp Ala Gly Lys
        35                  40                  45
Asp Lys Ile Glu Lys Val Ser Ile Tyr Met Val Pro Gln Gly Gly Pro
    50                  55                  60
Gly Leu Val Glu Ser Ala Glu Asp Leu Asp Phe Ser Thr Tyr Tyr Asp
65                  70                  75                  80
Ala Pro Thr Gln Asp Pro Gly Ser Asn Asn Val Ile Leu Lys Pro Lys
                85                  90                  95
Lys Gly Ile Lys Val Asn Ser Ala Val Gly Lys Thr Val Lys Val Tyr
            100                 105                 110
Val Val Leu Asn Asp Ile Ala Gly Lys Ala Lys Ala Leu Leu Ala Asn
        115                 120                 125
Val Asn Ala Ala Asp Phe Asp Ala Lys Phe Lys Glu Val Ile Glu Leu
    130                 135                 140
Ser Thr Gln Ala Glu Ala Val Ser Gln Ala Asn Ala Phe Asn Gly Thr
145                 150                 155                 160
Ala Ala Gly Lys Ile Ala Lys Lys Asn Gly Ala Thr Asp Glu Thr Ile
                165                 170                 175
Met Met Thr Cys Leu Gln Pro Ser Asp Ala Leu Thr Ile Glu Ala Ala
            180                 185                 190
Val Ser Glu Ala Asn Ala Ile Ala Gly Val Lys Asn Gln Ala Lys Val
        195                 200                 205
Thr Val Glu Arg Ser Val Ala Arg Ala Met Leu Ser Thr Lys Ala Asp
    210                 215                 220
Thr Phe Glu Ile Leu Ala Ala Asn Gln Ile Gly Ile Ala Ala Gly
225                 230                 235                 240
Ser Val Leu Ala Thr Ile Thr Asp Ile Arg Trp Val Val Ala Gln Gly
                245                 250                 255
Glu Arg Arg Gln Tyr Leu Ser Lys Lys Arg Gly Thr Ile Gln Glu Asn
            260                 265                 270
Thr Trp Val Thr Pro Gly Ser Asp Phe Val Pro Thr Ser Ser Thr Phe
        275                 280                 285
```

His Thr Asn Ala Thr Glu Tyr Tyr Asp Tyr Ala Gly Trp Glu Asp His
    290                 295                 300

Asn Thr Asp Pro Thr Val Ile Ser Gly Thr Gln Val Pro Thr Leu Ala
305                 310                 315                 320

Asp Tyr Gln Leu Gln Asn Val Thr Asp Glu Leu Ala Gln Ser Leu Ser
                    325                 330                 335

Gly Lys Phe Leu Leu Pro Asn Thr His Lys Ser Gly Thr Asp Ala Ala
                340                 345                 350

Thr Ser His Tyr Lys Arg Gly Asn Thr Ala Tyr Val Leu Ile Arg Ala
            355                 360                 365

Lys Phe Thr Pro Lys Lys Glu Ala Phe Ile Asp Lys Gly Lys Thr Tyr
        370                 375                 380

Thr Asp Gly Thr Gln Val Pro Glu Tyr Glu Ala Asp Gln Asp Phe Phe
385                 390                 395                 400

Val Gly Glu Asn Gly Gln Phe Tyr Val Ser Met Lys Ser Val Thr Asp
                    405                 410                 415

Pro Lys Val Gly Gly Val Thr Gly Met Lys Ala His Lys Tyr Val Lys
                420                 425                 430

Gly Lys Val Leu Tyr Tyr Ala Trp Leu Asn Pro Ser Thr Thr Ser Pro
            435                 440                 445

Asp Thr Trp Asn Ser Pro Val Val Arg Asn Asn Ile Tyr His Ile
        450                 455                 460

His Ile Lys Ser Ile Lys Lys Leu Gly Phe Asn Trp Asn Pro Leu Val
465                 470                 475                 480

Pro Asp Pro Asn Pro Asn Asp Pro Val Asn Pro Asn Pro Asp Pro
                    485                 490                 495

Asn Pro Asp Glu Pro Gly Thr Pro Val Pro Thr Asp Pro Glu Gln
                500                 505                 510

Pro Leu Pro Asp Gln Asp Thr Phe Met Ser Val Glu Val Thr Val Leu
            515                 520                 525

Pro Trp Lys Val His Ser Tyr Glu Val Asp Leu
        530                 535

<210> SEQ ID NO 5
<211> LENGTH: 166
<212> TYPE: PRT
<213> ORGANISM: Porphyromonas gulae
<223> OTHER INFORMATION: Gingipain HA1

<400> SEQUENCE: 5

Met Thr Glu Ser Phe Asp Gly Gly Ile Pro Ala Thr Trp Thr Leu Ile
1               5                   10                  15

Asp Ala Asp Gly Asp Gly His Gly Trp Lys His Gly Lys Ala Pro Gly
                20                  25                  30

Val Ala Gly Tyr Asn Ser Asn Gly Cys Val Tyr Ser Glu Ser Phe Gly
            35                  40                  45

Leu Gly Gly Ile Gly Val Leu Thr Pro Asp Asn Tyr Leu Ile Thr Pro
        50                  55                  60

Ala Leu Asn Leu Pro Asn Gly Gly Lys Leu Thr Phe Trp Val Cys Ala
65                  70                  75                  80

Gln Asp Ala Ala Tyr Ala Ser Glu His Tyr Ala Val Tyr Ala Ser Ser
                    85                  90                  95

Thr Gly Asn Ala Ala Ser Asn Phe Thr Asn Ala Leu Leu Glu Glu Thr
                100                 105                 110

Leu Thr Ala Lys Gly Val Arg Ser Pro Glu Ala Ile Arg Gly Arg Val

```
                    115                 120                 125
Gln Gly Thr Trp Tyr Gln Lys Thr Val Asp Leu Pro Ala Gly Thr Lys
    130                 135                 140

Tyr Val Ala Phe Arg His Phe Gln Ser Thr Asp Met Phe Tyr Ile Asp
145                 150                 155                 160

Ile Asp Glu Val Glu Ile
                165

<210> SEQ ID NO 6
<211> LENGTH: 173
<212> TYPE: PRT
<213> ORGANISM: Porphyromonas gulae
<223> OTHER INFORMATION: Gingipain HA2

<400> SEQUENCE: 6

Met Asn Ala Lys Arg Ser Glu Leu Leu Asn Glu Asn Phe Glu Gly Asp
1               5                   10                  15

Asp Ile Pro Ala Gly Trp Thr Ala Leu Asp Ala Asp Gly Asp Gly Asn
                20                  25                  30

Asn Trp Gly Val Gln Leu Asn Gln Phe Thr Arg Gly Glu Arg Glu Ala
        35                  40                  45

Leu Ala Pro Leu Arg Ala Ser Asn Val Ala Ile Ser Tyr Ser Ser Leu
    50                  55                  60

Asn Gln Gly Gly Gly Tyr Leu Pro Leu Thr Pro Asn Asn Phe Leu Ile
65                  70                  75                  80

Thr Pro Lys Val Glu Gly Ala Lys Lys Ile Ser Tyr Lys Val Gly Ser
                85                  90                  95

Pro Gly Asn Gln Ser Trp Ser His Asp His Tyr Ala Leu Cys Ile Ser
            100                 105                 110

Lys Thr Gly Thr Ala Ala Ser Asp Phe Glu Ile Ile Phe Glu Glu Thr
        115                 120                 125

Met Val Tyr Ser Gln Gly Gly Ala Asn Phe Thr Arg Glu Lys Asp Leu
    130                 135                 140

Pro Asp Gly Thr Lys Tyr Val Ala Phe Arg His Tyr Asn Cys Thr Asp
145                 150                 155                 160

Val Leu Ala Ile Val Ile Asp Asp Val Val Ile Thr Gly
                165                 170
```

PERIODONTITIS VACCINE AND RELATED COMPOSITIONS AND METHODS OF USE

CROSS-REFERENCE TO RELATED APPLICATIONS

This application claims priority under 35 U.S.C. § 119(e)(1) to provisional U.S. Patent Application Ser. No. 62/571,582, filed Oct. 12, 2017, the disclosure of which is incorporated by reference herein.

SEQUENCE LISTING

The instant application contains a Sequence Listing which has been submitted in ASCII format via EFS-Web and is hereby incorporated by reference in its entirety. Said ASCII copy, created on Feb. 27, 2019 is named "20190227 3369-00-001U01 Sequence Listing" and is 17.7 kilobytes in size.

TECHNICAL FIELD

The present invention relates generally to the prevention and treatment of periodontitis, and more particularly relates to a periodontal vaccine composition and a method for its use.

BACKGROUND

Periodontal diseases, collectively referred to as "periodontitis," are commonly occurring, yet complex chronic oral inflammatory diseases that destroy the soft and hard tissues supporting the teeth. If left untreated, the loss of the alveolar bone around the teeth can result in the loosening and subsequent loss of teeth. Periodontal disease is among the most common human diseases of bacterial origin, with recent studies indicating that approximately 60% of individuals over 40 years of age in the United States have moderate or severe periodontitis and possess measurable oral bone loss. The prevalence of periodontitis increases with age; see Eke et al. (2012) *J. Dent. Res.* 91(10): 914-920. Severe generalized periodontal disease occurs in an estimated 5-20% of individuals globally (Burt et al. (2005) *J. Periodontol.* 76(8): 1406-19, often resulting in multiple tooth loss by middle age, and the economic burden of this disease is significant, with 2010 data estimating the economic impact at $54 billion in the US alone (Listl et al. (2015) *J. Dent. Res.* 94(10): 1355-61.

Periodontitis is characterized according to both severity and cause in a classification system with seven recognized major categories: (1) gingival disease, or "gingivitis," involving inflammation of the gingiva; (2) chronic periodontitis, a slowly progressive disease that may be either localized or generalized; (3) early onset, or "aggressive" periodontitis; (4) periodontitis associated with a systemic disease such as diabetes mellitus, AIDS, and leukemia; (5) necrotizing periodontal disease; (6) periodontal abscesses; and (7) periodontitis associated with endodontic lesions. The latter six categories are designated "destructive" periodontal diseases because the damage caused is irreversible. See Armitage (1999) *Ann. Periodontol.* 4(1): 1-6. The symptoms of periodontitis include inflamed or bleeding gums, gingival recession, pockets between the teeth and gums, and, in the case of severe periodontitis, loosening or loss of teeth. Treatments will depend on the extent and cause of the disease, and include scaling, root planing, antibiotic therapy, and surgery. Scaling and root planing often have to be carried out multiple times, antibiotic therapy can be problematic insofar as beneficial oral microbes can be killed along with the pathogenic bacteria, and oral surgery is a generally undesirable solution of last resort.

Periodontitis is initiated by the presence of keystone bacteria such as *Porphyromonas gingivalis*. *Porphyromonas* organisms possess an array of molecules contributing to its overall virulence, including fimbriae and gingipains (a group of cysteine proteases) that impact various aspects of disease pathogenesis including attachment of bacteria to cells and other community microbes, development of inflammation, and microbial dysbiosis associated with periodontal disease; see Lamont et al. (1998) *Microbiol. Mol. Biol. Rev.* 62(4): 1244-63, and Bostanci et al. (2012) *FEMS Microbiol. Lett.* 333(1): 1-9. Several of these bacterial virulence factors have been explored as potential targets for vaccine development. See, e.g., Lamont et al., supra; Arjunan et al. (2016) *Mol. Oral Microbiol.* 31(1): 78093; Takahashi et al. (2006) *Cell Microbiol.* 8(5):738-57; Malek et al. (1994) *J. Bacteriol.* 176(4): 1-52-9); Gibson et al. (2001) *Infect. Immun.* 69(12): 7959-63; and Evans et al. (1992) *Infect. Immun.* 60(7): 2926-35.

A vaccine to treat periodontitis—and possibly prevent periodontitis as well—would eliminate the need for repeated clinical interventions and/or oral surgery. Development of an effective therapeutic and/or prophylactic vaccine for periodontal disease would be especially useful as the disease occurs in a significant portion of the adult population. However, periodontitis is a multifactorial disease with factors including bacterial composition of dental plaque, host genetic make-up, and environmental factors contributing unique barriers to a basic understanding of periodontal disease pathogenesis and the potential for targeted vaccine development.

An ideal periodontitis vaccine would achieve therapeutic efficacy in subjects with periodontitis and be effective in the prophylactic context as well. The need for aggressive clinical interventions would be eliminated, and the number of individuals suffering from periodontal diseases would substantially decrease. In addition, an ideal vaccine would be straightforward to manufacture using a cost-effective process amenable to large-scale production.

SUMMARY OF THE INVENTION

The invention is addressed to the aforementioned need in the art and provides an immunogenic composition, a vaccine formulation comprising the composition, and methods for treating and preventing periodontal disease.

In a first embodiment of the invention, an immunogenic composition is provided comprising at least one polypeptide that comprises: (a) an Mfa1 antigen sequence that is substantially homologous to an immunogenic amino acid sequence from an Mfa1 fimbrilin protein of a *Porphyromonas* bacterium; and (b) an HA1 antigen sequence, an HA2 antigen sequence, or both an HA1 antigen sequence and an HA2 antigen sequence, wherein (i) the HA1 antigen sequence is substantially homologous to an immunogenic amino acid sequence from an RgpA Gingipain hemagglutinin domain 1 (also referred to herein as "Gingipain HA1" or "HA1") contained within an RgpA Gingipain protein of a *Porphyromonas* bacterium, and (ii) the HA2 antigen sequence is substantially homologous to an immunogenic amino acid sequence from an RgpA Gingipain hemagglutinin domain 2 (also referred to herein as "Gingipain HA1" or "HA1") contained within an RgpA Gingipain protein of a *Porphyromonas* bacterium.

In one aspect of this embodiment, the at least one polypeptide comprises a first polypeptide that comprises: (a) an Mfa1 antigen sequence and an HA1 antigen sequence; (b) an Mfa1 antigen sequence and an HA2 antigen sequence; or (c) an Mfa1 antigen sequence, an HA1 antigen sequence, and an HA2 antigen sequence. It will thus be appreciated that the first polypeptide may be a fusion protein that includes the Mfa1 antigen sequence as well as the HA1 antigen sequence and/or the HA2 antigen sequence. In a related aspect, the at least one polypeptide comprises (a) a first polypeptide comprising an Mfa1 antigen sequence; and (b) a second polypeptide comprising an HA1 antigen sequence, an HA2 antigen sequence, or both an HA1 antigen sequence and an HA2 antigen sequence. Thus, in this aspect the Mfa1 antigen sequence is within one polypeptide, and the HA1 and HA2 antigen sequences are within a second polypeptide, which is a fusion polypeptide if both are present.

In another aspect of this embodiment, the at least one polypeptide of the immunogenic composition comprises a first polypeptide comprising an Mfa1 antigen sequence, a second polypeptide comprising an HA1 antigen sequence, and a third polypeptide comprising an HA2 antigen sequence. Thus, in this aspect, there are three distinct polypeptides each containing one of the Mfa 1, HA1 and HA2 antigen sequences.

In a related aspect, the Mfa1 antigen sequence, the HA1 antigen sequence, and the HA2 antigen sequence are substantially homologous to an immunogenic amino acid sequence of the Mfa1 fimbrilin polypeptide, Gingipain HA1 and Gingipain HA2, respectively, of a *Porphyromonas* species selected from *P. gingivalis, P. gulae, P. cangingivalis, P. gingivicanis, P. canoris, P. salivosa*, and *P. circumdentaria*.

In another aspect of this embodiment, the Mfa1 antigen sequence, the HA1 antigen sequence, and the HA2 antigen sequence are substantially homologous to an immunogenic amino acid sequence of the Mfa1 fimbrilin polypeptide, Gingipain HA1 and Gingipain HA2, respectively, of *P. gingivalis*.

In another aspect of this embodiment, the Mfa1 antigen sequence, the HA1 antigen sequence, and the HA2 antigen sequence are substantially homologous to an immunogenic amino acid sequence of the Mfa1 fimbrilin polypeptide, Gingipain HA1 and Gingipain HA2, respectively, of *P. gulae*.

In another embodiment of the invention, a periodontitis vaccine formulation is provided that comprises an immunogenic composition as described above and a pharmaceutically acceptable excipient. In the usual instance, the formulation contains at least one excipient, where the at least one excipient is selected from vehicles, solubilizers, emulsifiers, stabilizers, preservatives, isotonicity agents, buffer systems, dispersants, diluents, viscosity modifiers, and absorption enhancers. The vaccine may, in addition or in the alternative, include at least one adjuvant.

In one aspect of this embodiment, the vaccine formulation is formulated as sterile injectable solution. In a related aspect of this embodiment, the vaccine formulation is formulated as a lyophilized composition to be rehydrated prior to use.

In another embodiment, a method is provided for immunizing a subject against periodontal disease by administering to the subject an immunologically effective amount of an immunogenic composition of the invention. In one aspect of this embodiment, the method involves treating periodontitis in a subject exhibiting symptoms of periodontitis. In another aspect of this embodiment, the method involves reducing the risk of periodontitis developing in a subject, who may have a predisposition to developing periodontitis, including moderate to severe periodontitis, where the predisposition is associated with a risk factor such as age, genetic predisposition, an immunocompromised state, a systemic disease that increases the risk of developing periodontitis, the presence of endodontic lesions or abscesses, or other risk factors. Examples of systemic diseases that increase the risk of developing moderate to severe periodontitis include diabetes mellitus, AIDS, leukemia, and Down's syndrome.

DETAILED DESCRIPTION OF THE INVENTION

1. Terminology and Definitions

Figure 1:
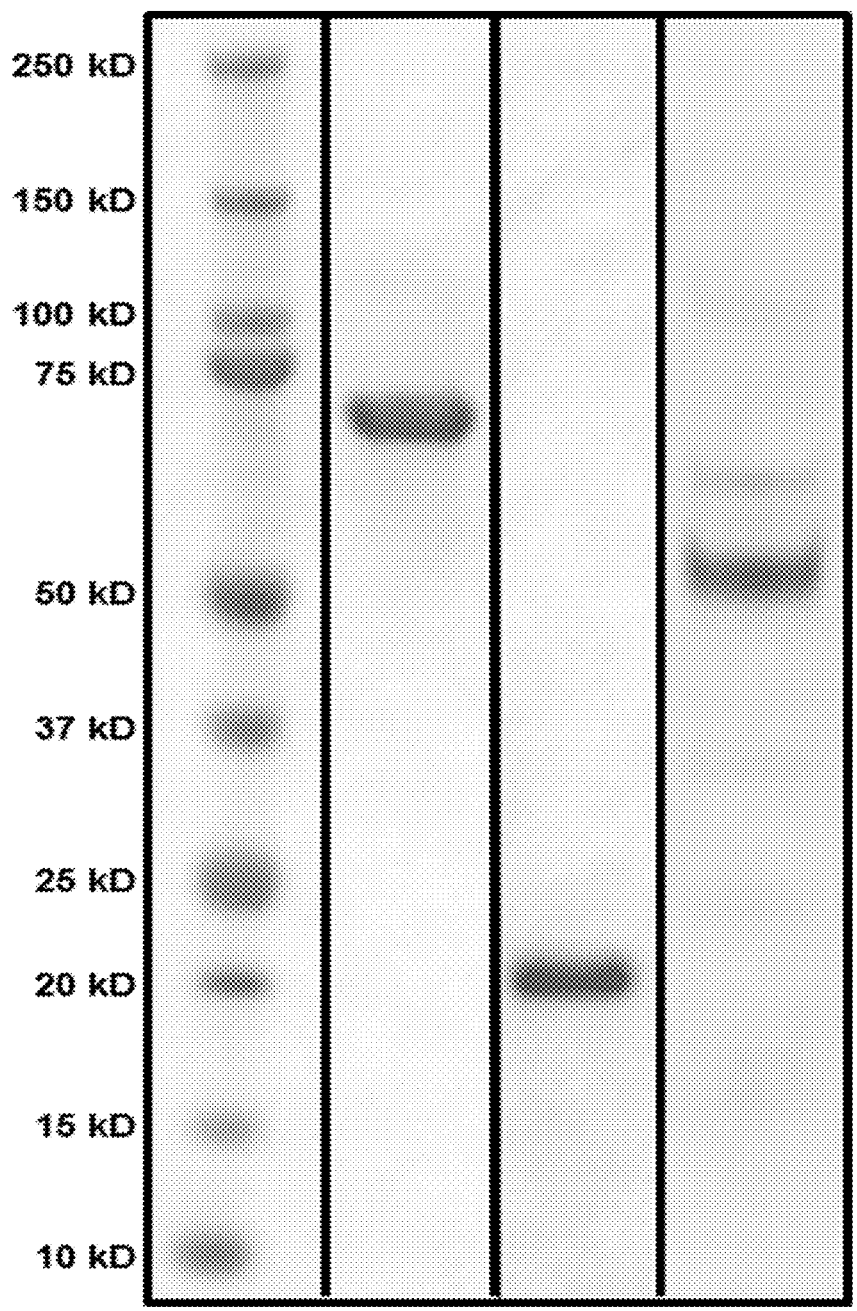
FIG. 1 provides the SDS-PAGE analysis of purified polypeptides Mfa1, HA1, and HA2 generated by cell-free protein synthesis.

Unless defined otherwise, all technical and scientific terms used herein have the meaning commonly understood by one of ordinary skill in the art to which the invention pertains. Specific terminology of particular importance to the description of the present invention is defined below.

In this specification and the appended claims, the singular forms "a," "an" and "the" include plural referents unless the context clearly dictates otherwise. Thus, for example, "a polypeptide" refers not only to a single polypeptide but also to a combination of two or more different polypeptides that may or may not be combined, "an adjuvant" refers to a single adjuvant as well as to two or more adjuvants that may be separate or combined in a single composition, and the like.

A "biomolecule," also referred to herein as a "biological molecule," is any organic molecule, whether naturally occurring, recombinantly produced, chemically synthesized in whole or in part, or chemically or biologically modified, that is, was or can be a part of a living organism. The term encompasses, for example, polypeptides, peptide fragments, amino acids, polysaccharides, lipids, and the like.

The term "polypeptide" is intended to include any structure comprised of one or more amino acids, and thus includes dipeptides, oligopeptides, polypeptides, polypeptide fragments, and proteins. The amino acids forming all or a part of a polypeptide may be any of the twenty conventional, naturally occurring amino acids, i.e., alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), and tyrosine (Y), as well as non-conventional amino acids such as isomers and modifications of the conventional amino acids, e.g., D-amino acids, non-protein amino acids, post-translationally modified amino acids, enzymatically modified amino acids, β-amino acids, constructs or structures designed to mimic amino acids (e.g., α,α-disubstituted amino acids, N-alkyl amino acids, lactic acid, β-alanine, naphthylalanine, 3-pyridylalanine, 4-hydroxyproline, O-phosphoserine, N-acetylserine, N-formylmethionine, 3-methylhistidine, 5-hydroxylysine, and nor-leucine), and other non-conventional amino acids, as described, for example, in U.S. Pat. No. 5,679,782 to Rosenberg et al. The polypeptides described herein may include one or more non-natural amino acids bearing a functional group that enables conjugation to a secondary antigen, e.g., a polysaccharide. Polypeptides can be (a) naturally occurring, (b) produced by chemical synthesis, (c) produced by recombinant DNA technology, (d) produced by biochemical or enzymatic fragmentation of larger molecules, (e) produced by methods resulting from a combination of methods (a) through (d) listed above, or (f) produced by any other means for producing peptides, such as cell-free protein synthesis, described infra.

The terms "sequence identity," "percent sequence homology," and "sequence homology," in the context of a polymeric biomolecule sequence, e.g., a polypeptide sequence, refer to two or more sequences that are the same or have a specified percentage of amino acid residues (or nucleotides, or other types of monomer units making up the polymeric biomolecule) that are the same, when compared and aligned for maximum correspondence over a given length (comparison window), as measured using a sequence comparison algorithm, e.g., BLASTP or the Smith-Waterman homology search algorithm. In the present context, the percent sequence homology may be determined over the full-length of the biomolecule or just a portion. One method for calculating percent sequence homology is the BLASTP program having its defaults set at a wordlength (W) of 3, an expectation (E) of 10, and the BLOSUM62 scoring matrix; see, e.g., Henikoff et al. (1989) Proc. Natl. Acad. Sci. USA 89:10915. Exemplary determination of sequence alignment and % sequence identity employs the BESTFIT or GAP programs in the GCG Wisconsin Software package (Accelrys, Madison Wis.), using the default parameters provided. If these preferred methods of calculating sequence identity give differing amounts, the method giving the higher sequence identity controls.

The term "substantially homologous" refers to a percent sequence homology over a given length (e.g., "x" amino acids of a polypeptide) of at least about 50%, thus including, for example, at least about 75%, at least about 80%, at least about 90%, at least about 95%, at least about 97%, at least about 99%, and 100%.

"Recombinant" polypeptides refer to polypeptides produced by recombinant DNA techniques, i.e., produced from cells transformed by an exogenous DNA construct encoding the desired polypeptide. "Synthetic" polypeptides are those prepared by chemical synthesis.

As used herein, the term "immunogenic" refers to the ability of an antigen (e.g., a polypeptide), to elicit an immune response, either a humoral or cellular immune response, and preferably both. In a preferred embodiment, the subject will display either a therapeutic or protective immunological response to administration of an "effective amount" or "immunologically effective amount" of an immunogenic composition herein such that resistance to new infection will be enhanced and/or the clinical severity of the periodontal disease will be reduced. The immunological response will normally be demonstrated by alleviation or elimination of at least one symptom associated with the infection.

As used herein, when the term "purified" is used in reference to a molecule, it means that the concentration of the molecule being purified has been increased relative to the concentration of the molecule in its natural environment. The term may also refer to purification of a chemically synthesized molecule from a reaction mixture in which the molecule has been generated as a reaction product. As used herein, when the term "isolated" is used in reference to a molecule, the term means that the molecule has been removed from its native environment. For example, a polynucleotide or a polypeptide naturally present in a living organism is not "isolated," but the same polynucleotide or polypeptide separated from the coexisting materials in its natural state is "isolated." An isolated moiety, whether separated from a native environment or from a non-natural environment (e.g., recombinant expression, cell-free expression, chemical synthesis, etc.), is preferably are at least about 1% pure, 5% pure, 10% pure, 20% pure, 30% pure, 40% pure, 50% pure, 60% pure, 70% pure, 80% pure, 90% pure, 95% pure, or 99% pure, or they may be 100% pure. As used herein, the term "% pure" indicates the percentage of a composition that is made up of the molecule of interest, by weight.

As used herein, the term "molecular weight" of a polypeptide or other biomolecule refers to molecular weight calculated by size exclusion chromatography (SEC) combined with multiangle laser light scattering (MALS).

The term "treating" refers to therapeutic treatment by the administration of an immunogenic composition or vaccine formulation of the invention, where the object is to lessen or eliminate infection. For example, "treating" may include directly affecting, suppressing, inhibiting, and eliminating infection, as well as reducing the severity of, delaying the onset of, and/or reducing symptoms associated with an infection. Unless otherwise indicated explicitly or implied by context, the term "treating" encompasses "preventing" (or prophylaxis or prophylactic treatment) where "preventing" may refer to reducing the risk that a subject will develop an infection, delaying the onset of symptoms, preventing relapse of an infection, or preventing the development of infection.

2. Immunogenic Composition and Vaccine Formulation

In a first embodiment of the invention, an immunogenic composition is provided that includes at least one polypeptide that comprises: (a) an Mfa1 antigen sequence that is substantially homologous to an immunogenic amino acid sequence from an Mfa1 fimbrilin protein of a *Porphyromonas* bacterium; and (b) an HA1 antigen sequence and/or an HA2 antigen sequence, wherein the HA1 antigen sequence is substantially homologous to an immunogenic amino acid sequence from a *Porphyromonas* Gingipain HA1 and the HA2 antigen sequence is substantially homologous to an immunogenic amino acid sequence from a *Porphyromonas* Gingipain HA2. The at least one polypeptide may be a fusion protein that contains the Mfa1 antigen sequence, the HA1 antigen sequence, and the HA2 antigen sequence. The at least one polypeptide may also be a fusion protein that contains the Mfa1 antigen sequence and the HA1 antigen sequence, or a fusion protein that contains the Mfa1 antigen sequence and the HA2 antigen sequence. In a variation on such an embodiment, the at least one polypeptide may comprise a first polypeptide that includes the Mfa1 antigen sequence, and a second polypeptide that includes either or both the HA1 antigen sequence and the HA2 antigen sequence.

In a preferred embodiment, however, the at least one polypeptide in the immunogenic composition comprises two distinct polypeptides: a first polypeptide containing the Mfa1 antigen sequence and a second polypeptide containing the HA1 antigen sequence or the HA2 antigen sequence. In another preferred embodiment, the at least one polypeptide in the immunogenic composition comprises three distinct polypeptides: a first polypeptide containing the Mfa1 antigen sequence, a second polypeptide containing the HA1 antigen sequence, and a third polypeptide containing the HA2 antigen sequence.

As discussed above, the Mfa1 antigen sequence is substantially homologous to an immunogenic amino acid sequence from an Mfa1 fimbrilin protein of a *Porphyromonas* bacterium, the HA1 antigen sequence is substantially homologous to an immunogenic amino acid sequence from a *Porphyromonas* Gingipain HA1 and the HA2 antigen sequence is substantially homologous to an immunogenic amino acid sequence from a *Porphyromonas* Gingipain HA2. The immunogenic sequences within these three antigens can collectively or individually be the full the full length protein or domain (i.e., Mfa 1 protein, RgpA Gingipain hemagglutinin domain 1, and/or RgpA Gingipain hemagglutinin domain 2), or a portion (or fragment) of such protein or domain so long as the portion selected results in compositions that possess the ability to generate a therapeutic or prophylactic immunogenic response to a *Porphyromonas* bacterium infection. Usually these immunogenic portions or fragments of the full protein or domain are at least 20 amino acid residues in length. Provided the desired immunogenic properties are maintained, the length of the protein or domain sequence upon which the antigen sequence is based is a matter of design choice and can be at least 20, 25, 30, 35, 40, 45, 50, 60, 70, 80, 90, or 100 amino acid residues, up to and including the full-length protein or domain. The antigenic sequences comprised within the polypeptides of the present invention are, therefore, substantially homologous to these immunogenic amino acid sequences from the full-length or portion of the native protein or domain sequences (i.e., Mfa1 fimbrilin protein, RgpA Gingipain hemagglutinin domain 1, and/or RgpA Gingipain hemagglutinin domain 2). Typically, usually for reasons related to the methodology or efficiency of polypeptide production, the antigenic sequences comprised within the polypeptides of the present invention are not exact copies of the native immunogenic sequence to which they correspond. For example, an N-terminal methionyl, which may be treated as outside the antigenic sequence to calculate maximum percent identity or homology, is often present due to the addition of a start codon. Additions, deletions and substitutions (often conservative substitutions) can also occur provided useful immunogenic properties are still present in the polypeptide. It can be appreciated, therefore, that the present invention may be carried out with polypeptides comprising (either within it or in its entirety) an amino acid residue sequence representing an antigenic sequence (i.e., the Mfa1 antigen sequence, HA1 antigen sequence, or HA2 antigen sequence) that is substantially homologous to an immunogenic amino acid residue sequence found within the corresponding protein or domain, wherein the immunogenic amino acid residue sequence is either the full-length protein or domain, or a portion or fragment thereof. These immunogenic amino acid residue sequences against which the substantial homology of the antigenic sequences are measured are individually either the full-length protein or domain, or a portion thereof that is at least 20, at least 25, at least 30, at least 35, at least 40, at least 45, at least 50, at least 60, at least 70, at least 80, at least 90, or 100 amino acid residues in length. Typically, these antigenic sequences are homologous to the immunogenic amino acid residue sequence against which the substantial homology of the antigenic sequence is measured at a level of at least 50%, at least 75%, at least 80%, at least 90%, at least 95%, at least 97%, at least 99%, or 100%. Routine testing in animals or humans can demonstrate readily whether compositions of the present invention based on portions of the full-length bacterial proteins or domains generate a therapeutic or prophylactic immunogenic response to infection by the bacteria in question.

Mfa1 fimbrilin protein is from a *Porphyromonas* bacterium, and the RgpA Gingipain hemagglutinin domains 1 and 2 are contained within an RgpA Gingipain protein that is also from a *Porphyromonas* bacterium, where the *Porphyromonas* bacterium may be any of various *Porphyromonas* species, including *P. gingivalis, P. gulae, P. cangingivalis, P. gingivicanis, P. canoris, P. salivosa*, and *P. circumdentaria*.

In a preferred embodiment, the Mfa1 fimbrilin protein is from *P. gingivalis*. Administration of an immunologically effective amount of a composition containing at least one polypeptide with an Mfa1 antigen sequence in this context will induce an immune response in which anti-Mfa1 antibodies are generated, disrupting one or more of the pathogenic pathways by which a *P. gingivalis* infection proceeds. In this embodiment, the Mfa1 antigen sequence is substantially homologous to an immunogenic amino acid sequence from an Mfa1 fimbrilin protein of a *P. gingivalis* bacterium, such as from the *P. gingivalis* Mfa1 fimbrilin protein having the amino acid of SEQ ID NO:1.

The *P. gingivalis* Mfa1 fimbrilin polypeptide, prepared as described in the Experimental Section, infra, contains 552 amino acids (this and following SEQ IDs include the addition of an N-terminal methionyl from a start codon used in the cell-free synthesis described below) and has a molecular weight of 60,018, with the amino acid sequence of SEQ ID NO: 1 reproduced for convenience below:

MGNGPDPDNAAKSYMSMTLSMPMGSARDGQNQDNPQYNFVGEWAGKDKIE

KVSIYMVPQGGPGLVESAEDLDFGTYYDAPTQEAGSNNVILKPKKGIKVN

SAVGKTVKVYVVLNDIAGKAKALLANVNAVDFEAKFKEVIELSTQAQALG

TVADGPNPATAAGKIAKKNGVDNETIMMTCFEPSAPLTIEAAVSEANAIA

GVKNQAKVTVERSVARAMVSTKAESYEIKATTQIGSIAAGDVLATVSDIR

WVVAQGERKQYLSKKRGTVPENTWVTPGSDYISTNANFHAQATMYYDYTG

LWDDHNADPTMVSGTKVPTLANYQLQDVTDELAQRLSGKFLLPNTHKSGI

DAATSHYKRGNTAYVLVRAKFTPKKEAFIDKGKDYTDGTPVPEYTDGDDF

FVGENGQFYVSMKSVTDPKVGGVAGMKAHKYVKGKVLYYAWLNPSTTSPD

SWWNSPVVRNNIYHIHIKSIKKLGFNWNPLVPNPQNPNDPNGPINPNNPD

PNPDEPGTPIPTDPEQPLPDQDTFMSVEVTVLPWKVHSYEVDL

In this embodiment, in which the Mfa1 antigen sequence is substantially homologous to an immunogenic amino acid sequence from an Mfa1 fimbrilin protein from *P. gingivalis*, it is preferred, although not essential, that the HA1 antigen sequence be substantially homologous to an immunogenic amino acid sequence from an RgpA Gingipain hemagglutinin domain 1 (HA1) contained within a *P. gingivalis* RgpA Gingipain protein, where, for example, the immunogenic amino acid sequence may be from the HA1 having SEQ ID NO: 2. Analogously, it is preferred, in this embodiment, that the HA2 antigen sequence be substantially homologous to an immunogenic amino acid sequence from an RgpA Gingipain hemagglutinin domain 2 (HA2) contained within a *P. gingivalis* RgpA Gingipain protein, where the immunogenic amino acid sequence may be from the HA2 having SEQ ID NO:3.

*P. gingivalis* Gingipain HA1 prepared as described infra, contains 176 amino acids and has a molecular weight of 19,059, with the amino acid sequence of SEQ ID NO: 2 reproduced for convenience below:

MLSESFENGIPASWKTIDADGDGHGWKPGNAPGIAGYNSNGCVYSESFGL

GGIGVLTPDNYLITPALDLPNGGKLTFWVCAQDANYASEHYAVYASSTGN

DASNFTNALLEETITAKGVRSPEAIRGRIQGTWRQKTVDLPAGTKYVAFR

HFQSTDMFYIDLDEVEI

*P. gingivalis* Gingipain HA2, also prepared as described infra, contains 442 amino acids and has a molecular weight of 48,299, with the amino acid sequence of SEQ ID NO: 3, reproduced below:

MFTETFESSTHGEAPAEWTTIDADGDGQDWLCLSSGQLDWLTAHGGTNVV

ASFSWNGMALNPDNYLISKDVTGATKVKYYYAVNDGFPGDHYAVMISKTG

TNAGDFTVVFEETPNGINKGGARFGLSTEANGAKPQSVWIERTVDLPAGT

KYVAFRHYNCSDLNYILLDDIQFTMGGSPTPTDYTYTVYRDGTKIKEGLT

ETTFEEDGVATGNHEYCVEVKYTAGVSPKVCVNVTINPTQFNPVKNLKAQ

PDGGDVVLKWEAPSGKRGELLNEDFEGDAIPTGWTALDADGDGNNWDITL

NEFTRGERHVLSPLRASNVAISYSSLLQGQEYLPLTPNNFLITPKVEGAK

KITYKVGSPGLPQWSHDHYALCISKSGTAAADFEVIFEETMTYTQGGANL

TREKDLPAGTKYVAFRHYNCTDVLGIMIDDVVI

Combining the Mfa1 antigen sequence with either or both the HA1 antigen sequence and the HA2 antigen sequence in one or more polypeptides in a single immunogenic composition is believed to target multiple mechanisms involved in the pathogenic progression of periodontal disease associated with *Porphyromonas* infection, i.e., mechanisms associated with the Mfa1 fimbrilin protein as well as the RgpA gingipain proteins.

In another embodiment, the Mfa1 fimbrilin protein is from *P. gulae*. In this case, the Mfa1 antigen sequence is substantially homologous to an immunogenic amino acid sequence from an Mfa1 fimbrilin protein of a *P. gulae* bacterium, such as from the *P. gulae* Mfa1 fimbrilin protein having the amino acid of SEQ ID NO:4. As explained with respect to *P. gingivalis*, the HA1 antigen sequence and the HA2 antigen sequence should be substantially homologous to immunogenic amino acid sequences from an RgpA hemagglutinin domain 1 and an RgpA hemagglutinin domain 2, respectively, contained within an RgpA Gingipain protein of a *P. gulae* organism. The immunogenic amino acid sequence from the *P. gulae* HA1 may be from SEQ ID NO: 5, and the immunogenic amino acid sequence from the *P. gulae* HA2 may be from SEQ ID NO: 6.

*P. gulae* Mfa1 fimbrilin polypeptide (SEQ ID NO: 4):
MGNGPDPDNAAKSYMSMTLSMPLGSARAGDGQDQPNPDYNYVGEWAGKDK

IEKVSIYMVPQGGPGLVESAEDLDFSTYYDAPTQDPGSNNVILKPKKGIK

VNSAVGKTVKVYVVLNDIAGKAKALLANVNAADFDAKF KEVIELSTQAE

AVSQANAFNGTAAGKIAKKNGATDETIMMTCLQPSDALTIEAAVSEANAI

AGVKNQAKVTVERSVARAMLSTKADTFEILAANQIGEIAAGSVLATITDI

RWVVAQGERRQYLSKKRGTIQENTWVTPGSDFVPTSSTFHTNATEYYDYA

GWEDHNTDPTVISGTQVPTLADYQLQNVTDELAQSLSGKFLLPNTHKSGT

DAATSHYKRGNTAYVLIRAKFTPKKEAFIDKGKTYTDGTQVPEYEADQDF

FVGENGQFYVSMKSVTDPKVGGVTGMKAHKYVKGKVLYYAWLNPSTTSPD

TWWNSPVVRNNIYHIHIKSIKKLGFNWNPLVPDPNPNDPVNPNNPDPNPD

EPGTPVPTDDPEQPLPDQDTFMSVEVTVLPWKVHSYEVDL

*P. gulae* Gingipain HA1 (SEQ ID NO: 5):
MTESFDGGIPATWTLIDADGDGHGWKHGKAPGVAGYNSNGCVYSESFGLG

GIGVLTPDNYLITPALNLPNGGKLTFWVCAQDAAYASEHYAVYASSTGNA

ASNFTNALLEETLTAKGVRSPEAIRGRVQGTWYQKTVDLPAGTKYVAFRH

FQSTDMFYIDIDEVEI

*P. gulae* Gingipain HA2 (SEQ ID NO: 6):
MNAKRSELLNENFEGDDIPAGWTALDADGDGNNWGVQLNQFTRGEREALA

PLRASNVAISYSSLNQGGGYLPLTPNNFLITPKVEGAKKISYKVGSPGNQ

SWSHDHYALCISKTGTAASDFEIIFEETMVYSQGGANFTREKDLPDGTKY

VAFRHYNCTDVLAIVIDDVVITG

The present immunogenic compositions thus include:

(1) an immunogenic composition comprising (a) a *P. gingivalis* Mfa1 antigen sequence that is substantially homologous to an immunogenic amino acid sequence from *P. gingivalis* Mfa1 fimbrilin protein having SEQ ID NO: 1, and (b) a *P. gingivalis* HA1 antigen sequence that is substantially homologous to an immunogenic amino acid sequence from *P. gingivalis* Gingipain HA1 SEQ ID NO: 2;

(2) an immunogenic composition comprising (a) a *P. gingivalis* Mfa1 antigen sequence that is substantially homologous to an immunogenic amino acid sequence from *P. gingivalis* Mfa1 fimbrilin protein having SEQ ID NO: 1, and (b) a *P. gingivalis* HA2 antigen sequence that is substantially homologous to an immunogenic amino acid sequence from *P. gingivalis* Gingipain HA2, SEQ ID NO: 3;

(3) an immunogenic composition comprising (a) a *P. gingivalis* Mfa1 antigen sequence that is substantially homologous to an immunogenic amino acid sequence from *P. gingivalis* Mfa1 fimbrilin protein having SEQ ID NO: 1, (b) a *P. gingivalis* HA1 antigen sequence that is substantially homologous to an immunogenic amino acid sequence from *P. gingivalis* Gingipain HA1 SEQ ID NO: 2, and (c) a *P. gingivalis* HA2 antigen sequence that is substantially homologous to an immunogenic amino acid sequence from *P. gingivalis* Gingipain HA2, SEQ ID NO: 3;

(4) an immunogenic composition comprising (a) a *P. gulae* Mfa1 antigen sequence that is substantially homologous to an immunogenic amino acid sequence from *P. gulae* Mfa1 fimbrilin protein having SEQ ID NO: 4, and (b) a *P. gulae* HA1 antigen sequence that is substantially homologous to an immunogenic amino acid sequence from *P. gulae* Gingipain HA1 SEQ ID NO: 5;

(5) an immunogenic composition comprising (a) a *P. gulae* Mfa1 antigen sequence that is substantially homologous to an immunogenic amino acid sequence from *P. gulae* Mfa1 fimbrilin protein having SEQ ID NO: 4, and (b) a *P. gulae* HA2 antigen sequence that is substantially homologous to an immunogenic amino acid sequence from *P. gulae* Gingipain HA1 SEQ ID NO: 6; and (6) an immunogenic composition comprising (a) a *P. gulae* Mfa1 antigen sequence that is substantially homologous to an immunogenic amino acid sequence from *P. gulae* Mfa1 fimbrilin protein having SEQ ID NO: 4, (b) a *P. gulae* HA antigen sequence that is substantially homologous to an immunogenic amino acid sequence from *P. gulae* Gingipain HA1 SEQ ID NO: 5, and (c) a *P. gulae* HA2 antigen sequence that is substantially homologous to an immunogenic amino acid sequence from *P. gulae* Gingipain HA1 SEQ ID NO: 6.

In a preferred embodiment, the composition comprises an immunogenic composition suitable for incorporation into a vaccine formulation. At least one polypeptide containing a selected antigen sequence, as described above, is preferably incorporated into the composition in isolated or purified form, where the terms "isolated" and "purified" are defined earlier herein. The amount of the at least one polypeptide in the immunogenic composition is a sufficient and effective amount to generate a therapeutic or prophylactic immune response in a subject, i.e., an amount rendering the composition as a whole immunogenic. Thus, administration of an immunologically effective dose of the immunogenic composition to a subject, in a vaccine formulation, will elicit an immune response as explained in part (I) of this section, preferably a response that serves to inhibit the progression of, or prevent the onset of, periodontal disease associated with a *Porphyromonas* infection. The relative amounts of each polypeptide in the composition may vary a great deal. However, the composition is generally formulated with the selected polypeptides—for example, (a) a first polypeptide comprising the Mfa1 antigen sequence and a second polypeptide comprising the HA1 antigen sequence, the HA2 antigen sequence, or both; or (b) a first polypeptide comprising the Mfa1 antigen sequence, a second polypeptide comprising the HA1 antigen sequence, and a third polypeptide comprising the HA2 antigen sequence—combined in amounts corresponding to a weight ratio of each polypeptide in the composition to each other polypeptide in the composition in the range of about 1:5 to about 5:1, typically in the range of about 1:3 to about 3:1, for example in the range of about 1:1.5 to about 1.5:1, including about 1:1. In a preferred embodiment, the weight ratio of each polypeptide in the composition to each other polypeptide in the composition is in the range of 1:5 to 5:1, typically 1:3 to 3:1, such as 1:1.5 to 1.5:1, and including 1:1. Accordingly, the immunogenic composition may be one of the following:

(1) a composition formulated by combining a first polypeptide comprising the Mfa1 antigen sequence and a second polypeptide comprising the HA1 antigen sequence in a weight ratio ranging from 1:5 to 5:1;

(2) a composition formulated by combining a first polypeptide comprising the Mfa1 antigen sequence and a second polypeptide comprising the HA1 antigen sequence in a weight ratio ranging from 1:3 to 3:1;

(3) a composition formulated by combining a first polypeptide comprising the Mfa1 antigen sequence and a second polypeptide comprising the HA1 antigen sequence in a weight ratio ranging from 1:1.5 to 1.5:1;

(4) a composition formulated by combining a first polypeptide comprising the Mfa1 antigen sequence and a second polypeptide comprising the HA1 antigen sequence in a weight ratio of about 1:1;

(5) a composition formulated by combining a first polypeptide comprising the Mfa1 antigen sequence and a second polypeptide comprising the HA2 antigen sequence in a weight ratio ranging from 1:5 to 5:1;

(6) a composition formulated by combining a first polypeptide comprising the Mfa1 antigen sequence and a second polypeptide comprising the HA2 antigen sequence in a weight ratio ranging from 1:3 to 3:1;

(7) a composition formulated by combining a first polypeptide comprising the Mfa1 antigen sequence and a second polypeptide comprising the HA2 antigen sequence in a weight ratio ranging from 1:1.5 to 1.5:1;

(8) a composition formulated by combining a first polypeptide comprising the Mfa1 antigen sequence and a second polypeptide comprising the HA2 antigen sequence in a weight ratio of about 1:1;

(9) a composition formulated by combining a first polypeptide comprising the Mfa1 antigen sequence, a second polypeptide comprising the HA1 antigen sequence, and a third polypeptide comprising the HA2 antigen sequence, wherein the weight ratio of each polypeptide in the composition to each other polypeptide in the composition is in the range of 1:5 to 5:1;

(10) a composition formulated by combining a first polypeptide comprising the Mfa1 antigen sequence, a second polypeptide comprising the HA1 antigen sequence, and a third polypeptide comprising the HA2 antigen sequence, wherein the weight ratio of each polypeptide in the composition to each other polypeptide in the composition is in the range of 1:3 to 3:1;

(11) a composition formulated by combining a first polypeptide comprising the Mfa1 antigen sequence, a second polypeptide comprising the HA1 antigen sequence, and a third polypeptide comprising the HA2 antigen sequence, wherein the weight ratio of each polypeptide in the composition to each other polypeptide in the composition is in the range of 1:1.5 to 1.5:1; and

(12) a composition formulated by combining a first polypeptide comprising the Mfa1 antigen sequence, a second polypeptide comprising the HA1 antigen sequence, and a third polypeptide comprising the HA2 antigen sequence, wherein the weight ratio of each polypeptide in the composition to each other polypeptide in the composition is about 1:1, such that the weight ratios of the three polypeptides are about 1:1:1.

Additional antigens: In addition to the at least one polypeptide comprising the Mfa1 antigen sequence and the HA1 antigen sequence and/or the HA2 antigen sequence, the immunogenic composition may contain one or more additional antigens. An additional antigen may be one that induces an antibody response that targets *Porphyromonas* pathogenic mechanisms and/or virulence factors, for example, the bacterial tyrosine kinase Ptk1 (see Bainbridge (2010) *Infect. Immun.* 78(11): 4560-69) or the phosphoserine phosphatase enzyme SerB (see Wright et al. (2014) (*MicrobiologyOpen* 3(3): 383-94. Antigens may also be included in the composition that are directed toward pathogens other than *Porphyromonas* organisms, such as organisms that tend to be present in the multimicrobial biofilm associated with the progression of periodontal disease.

The at least one polypeptide of the immunogenic composition can be prepared in many ways, e.g., by solid phase or liquid phase chemical synthesis (in whole or in part), by digestion of longer polypeptides using proteases, by cell-based recombinant protein expression, by purification from a cell culture (e.g. from recombinant expression), etc. A preferred method for preparing the polypeptides, however, is the scalable cell-free protein synthesis ("CFPS") system, described in U.S. Pat. No. 9,040,253 to Roy et al., U.S. Pat. No. 9,650,621 to Thanos et al., and Murray et al. (2013) *Current Opin. Chem. Biol.* 17(3): 420-26, all of which are incorporated by reference herein. Cell-free synthesis of the Mfa1, HA1 and HA2 polypeptide antigens is described in detail in the Examples below.

The invention also provides a vaccine formulation that comprises the immunogenic composition in a sterile formulation for administration to a subject, e.g., as a suspension, solution or in lyophilized form to be rehydrated prior to use. The vaccine formulation includes the at least one polypeptide comprising the Mfa1 antigen sequence and the HA1 antigen sequence and/or the HA2 antigen sequence; optional additional antigens as explained above; and at least one additional component selected from adjuvants and excipients, as follows:

Adjuvants: The vaccine formulation may contain one or more adjuvants to potentiate the immune response to one or more antigens in the immunogenic composition. Suitable vaccine adjuvants for incorporation into the present formulation are described in the pertinent texts and literature and will be apparent to those of ordinary skill in the art. The major adjuvant groups are as follows:

Mineral salt adjuvants, including alum-based adjuvants such as aluminum phosphate, aluminum hydroxide, and aluminum sulfate, as well as other mineral salt adjuvants such as the phosphate, hydroxide, and sulfate salts of calcium, iron, and zirconium;

Saponin formulations, including the Quillaia saponin Quil A and the Quil A-derived saponin QS-21, as well as immune stimulating complexes (ISCOMs) formed upon admixture of cholesterol, phospholipid, and a saponin;

Bacteria-derived and bacteria-related adjuvants, including, without limitation, cell wall peptidoglycans and lipopolysaccharides derived from Gram negative bacteria such as *Mycobacterium* spp., *Corynebacterium parvum, C. granulosum, Bordetella pertussis*, and *Neisseria meningitis*, such as Lipid A, monophosphoryl Lipid A (MPLA), other Lipid A derivatives and mimetics (e.g., RC529), enterobacterial lipopolysaccharide ("LPS"), TLR4 ligands, and trehalose dimycolate ("TDM");

Muramyl peptides such as N-acetyl muramyl-L-alanyl-D-isoglutamine ("MDP") and MDP analogs and derivatives, e.g., threonyl-MDP and nor-MDP;

Oil-based adjuvants, including oil-in-water (O/W) and water-in-oil (W/O) emulsions, such as squalene-water emulsions (e.g., MF59, AS03, AF03), complete Freund's adjuvant ("CFA") and incomplete Freund's adjuvant ("IFA");

Liposome adjuvants;

Microsphere adjuvants formed from biodegradable and non-toxic polymers such as a poly($\alpha$-hydroxy acid), a poly (hydroxy butyric) acid, a polyorthoester, a polyanhydride, a polycaprolactone, etc.;

Human immunomodulators, including cytokines, such as interleukins (e.g. IL-1, IL-2, IL-4, IL-5, IL-6, IL-7, IL-12), interferons (e.g. interferon-$\gamma$), macrophage colony stimulating factor, and tumor necrosis factor;

Bioadhesives and mucoadhesives, such as chitosan and derivatives thereof and esterified hyaluronic acid and microspheres or mucoadhesives, such as cross-linked derivatives of poly(acrylic acid), polyvinyl alcohol, polyvinyl pyrrolidone, polysaccharides and carboxymethylcellulose;

Imidazoquinolone compounds, including Imiquamod and homologues thereof, e.g., Resiquimod;

TLR-9 agonists, such as Hsp90 and oligodeoxynucleotides containing unmethylated CpG motifs (see, e.g., Bode et al. (2011) Expert Rev. Vaccines 10(4): 499-511); and Carbohydrate adjuvants, including the inulin-derived adjuvants gamma inulin and algammulin, and other carbohydrate adjuvants such as polysaccharides based on glucose and mannose, including glucans, dextrans, lentinans, glucomannans, galactomannans, levans, and xylans.

Exemplary adjuvants herein include alum-based salts such as aluminum phosphate and aluminum hydroxide.

The vaccine formulation also includes at least one excipient, and usually two or more excipients, to serve any of a number of functions, where the excipients are immunologically and pharmacologically inert components that are "pharmaceutically acceptable." A "pharmaceutically acceptable" component herein is one that (1) can be included in a vaccine formulation administered to a subject without causing significant unwanted biological effects or interacting in a deleterious manner with any of the other components of the formulation; and (2) meets the criteria set out in the Inactive Ingredient prepared by the U.S. Food and Drug Administration, and, preferably, has also been designated "Generally Regarded as Safe" ("GRAS"). The type of excipient or excipients incorporated into a vaccine formulation herein will depend, in part, on the selected mode of administration and the particular formulation type or dosage form, e.g., injectable liquid formulations, intranasal spray formulations, or the like; modes of administration and corresponding formulations are discussed infra. In general, however, inert components that can be advantageously incorporated into the vaccine formulation of the invention include, without limitation, vehicles, solubilizers, emulsifiers, stabilizers, preservatives, isotonicity agents, buffer systems, dispersants, diluents, viscosity modifiers, absorption enhancers, and combinations thereof. A thorough discussion of pharmaceutically acceptable inert additives is available in Gennaro (2000) Remington: The Science and Practice of Pharmacy. 20th ed., ISBN: 0683306472.

3. Administration and Use

The immunogenic composition of the invention is useful in a method for immunizing a subject against periodontal disease, where the method involves administering to the subject an immunologically effective amount of a periodontal vaccine formulation comprising an immunogenic composition as described herein.

The subject may be a human or a non-human mammal, and the selection of target bacterium (which will be the source of the immunogenic amino acid sequences to which the antigen sequences correspond) may depend on the type of subject. For example, an immunogenic composition according to the present invention used to treat or prevent periodontitis in a human subject will typically be targeted to *P. gingivalis*. As another example, an immunogenic composition according to the present invention used to treat or prevent periodontitis in a non-human mammal, where such subjects may be dogs, horses, dairy cattle, cats, or other mammals, will generally be targeted to *P. gulae*.

The method may involve administration of the immunogenic composition as a therapeutic vaccine, i.e., to treat a subject suffering from periodontitis. The method may also involve administration of the immunogenic composition as a prophylactic vaccine, meaning that, for example, the method reduces the risk of periodontitis (including moderate to severe periodontitis) developing in a subject and thus may postpone or eliminate development of periodontitis. When the vaccine is used prophylactically, the subject may be predisposed to developing periodontitis as a result of any number of risk factors, including age; a genetic predisposition; an immunocompromised state; a disease that increases the risk of developing moderate to severe periodontitis, such as diabetes mellitus, AIDS, leukemia, Down's syndrome; or the presence of endodontic lesions or abscesses. As an example, patients receiving anti-TNF therapy (i.e., taking a TNF inhibitor such as etanercept or adalimumab), such as in the treatment of rheumatoid arthritis or psoriasis, often exhibit gingival inflammation and have an elevated risk of developing periodontitis.

The "immunologically effective amount" of the vaccine formulation is an amount that, either as a single dose or as part of a series of two or more doses, is effective for treating or preventing periodontal disease, where "treating" and "preventing" are defined in part (1) of this section. The amount administered will vary according to several factors, including the overall health and physical condition of the subject, the subject's age, the capacity of the subject's immune system to synthesize relevant antibodies, the form of the composition (e.g., injectable liquid, nasal spray, etc.), the taxonomic group of the subject (e.g., human, non-human primate, non-primates, etc.), and other factors known to the medical practitioner overseeing administration.

Administration of the immunogenic composition as a vaccine formulation can be carried out using any effective mode of systemic delivery. The composition is usually administered parenterally, such as by injection, including intravenous, intramuscular, intraperitoneal, interstitial, or subcutaneous injection; injection may also be gingival, in which case the vaccine formulation is injected directly into the gum. The composition may, in addition, be administered transmucosally, such as via the intranasal, sublingual, transbuccal, intravaginal, or intrarectal routes. Other modes of administration are also envisioned, however, and the invention is not limited in this regard. By way of example, other modes of administration include oral and transdermal delivery as well as administration via inhalation or using a subdermal implant.

The mode of administration largely dictates the type of formulation or dosage form that comprises the immunogenic composition. Compositions formulated for parenteral administration include sterile aqueous and nonaqueous solutions, suspensions, and emulsions. Injectable aqueous solutions contain the active agent in water-soluble form. Examples of nonaqueous solvents or vehicles include fatty oils, such as olive oil and corn oil, synthetic fatty acid esters, such as ethyl oleate or triglycerides, low molecular weight alcohols such as propylene glycol, synthetic hydrophilic polymers such as polyethylene glycol, liposomes, and the like. Parenteral formulations may also contain excipients such as solubilizers, emulsifiers, stabilizers, preservatives, isotonicity agents, buffer systems, dispersants, diluents, viscosity modifiers, absorption enhancers, and combinations thereof. Injectable formulations are rendered sterile by incorporation of a sterilizing agent, filtration through a bacteria-retaining filter, irradiation, or heat. They can also be manufactured using a sterile injectable medium. The immunogenic composition or individual components thereof may also be in dried, e.g., lyophilized, form that may be rehydrated with a suitable vehicle immediately prior to administration via injection.

Of the transmucosal routes, intranasal administration is generally although not necessarily preferred. Intranasal formulations, including intranasally administered vaccine formulations, are known in the art, and should be formulated with reference to the FDA's *Guidance for Industry: Nasal Spray and Inhalation Solution, Suspension, and Spray Drug Products*. Intranasal formulations are liquids, i.e., solutions, emulsions, suspensions, or the like, for administration as sprays, intranasal injections, or drops, and can contain adjuvants and pharmaceutically acceptable excipients as above. Because of the relatively large size of the antigens in the formulation, systemic delivery via the intranasal route requires incorporation of a transmucosal absorption enhancer in the immunogenic composition. Examples of suitable transmucosal absorption enhancers include, without limitation, alkylsaccharides, cyclodextrins, and chitosans; see Maggio (2014) *J. Excip. Food Chem.* 5(2): 100-12; and Merkus et al. (1999) *Adv. Drug Deliv. Rev.* 36: 41-57. The concentration of enhancer is selected to ensure that an immunologically effective amount of the formulation passes through the nasal membrane and into the systemic circulation at an efficient transport rate. Various anatomical and physiological considerations dictating the composition and nature of an intranasal vaccine formulation are discussed, for example, by Aurora (October 2002) *Drug Development & Delivery* 2(7), incorporated by reference herein.

Other modes of administration and corresponding formulations include, without limitation: sublingual administration with a rapidly dissolving dosage form such as a rapidly dissolving tablet; transbuccal administration using a buccal patch or other buccal delivery system; intravaginal administration using a pessary, ointment, or cream; intrarectal delivery using a rectal suppository, ointment, or cream; transdermal administration using a transdermal patch or formulation; subdermal administration with an injected implant or pellet; inhalation using a dry powder pulmonary formulation; and oral administration using an oral dosage form such as a tablet, capsule, or the like.

As alluded to earlier herein, the vaccine formulation is administered to a subject within the context of an appropriate dosage regimen. The composition may be administered once, or two or more times spaced out over an extended time period. For example, an initial, "prime" dose may be followed by at least one "boost" dose. The time interval between the prime and the subsequent boost dose, and between boost doses, is usually in the range of about 2 to about 24 weeks, more typically in the range of about 2 to 12 weeks, such as 2 to 8 weeks, 3-6 weeks, etc. Regardless of the mode of administration, e.g., intramuscular injection, gingival injection, intranasal administration, or the like, the volume of a single dose of the vaccine will generally be in the range of about 1 µL to about 500 µL, typically in the range of about 1 µL to about 250 µL, more typically in the range of about 2.5 µL to about 200 µL, and preferably in the range of about 5 µL to about 150 µL. It will be appreciated that the concentration of total antigen in the immunogenic composition corresponds to an immunologically effective dose of the composition per unit volume, working from the aforementioned dose volume guidelines.

For ease of use, the immunogenic composition of the invention can be incorporated into a packaged product, or "kit," including instructions for self-administration or administration by a medical practitioner. The kit includes a sealed container housing a dose of the vaccine formulation, typically a "unit dose" appropriate for a single dosage event that is immunologically effective. The vaccine may be in liquid form and thus ready to administer as an injection or the like, or it may be in another form that requires the user to perform a preparation process prior to administration, e.g., hydration of a lyophilized formulation, activation of an inert component, or the like. The kit may also include two or more sealed containers with the prime dose in a first container and a boost dose in one or more additional containers, or a periodontitis vaccine formulation in a first container and a vaccine directed against another infection, which may or may not be related to the *Porphyromonas* infection, in another container.

It is to be understood that while the invention has been described in conjunction with a number of specific embodiments, the foregoing description as well as the experimental section that follows are intended to illustrate and not limit the scope of the invention. In this regard, no attempt is made to show structural details of the invention in more detail than is necessary for the fundamental understanding of the invention, the description taken with the drawings and/or examples making apparent to those skilled in the art how the invention may be embodied in practice. This disclosure includes all modifications and equivalents of the subject matter recited in the claims appended hereto as permitted by applicable law. Moreover, any combination of the elements of the invention described herein are encompassed by the disclosure unless otherwise indicated herein or clearly contradicted by context.

Experimental

Generation of Cell Free Extract:

Cell free extracts containing additional DsbC chaperone were prepared as previously described by Groff et al. (2014) *Mabs* 7(1):231-242. Briefly, *E. coli* strain SBJY001(see Yin et al. (2012) *Mabs* 6(3):671-678) was transformed with a pACYC plasmid carrying tandem copies of the dsbC gene. Cells were grown, harvested and homogenized as described by Zawada et al. (2011) *Biotechnol. Bioeng.* 108(7):1570-1578. Subsequent clarification via centrifugation yielded the extract used for subsequent cell free expression reaction.

Generation of Recombinant *P. gingivalis* Mfa1, HA1, HA2, and Purification:

DNA sequences encoding the HA1 HA2 and Mfa1 fimbrilin proteins associated with *P. gingivalis* were codon optimized, synthesized (DNA 2.0; Menlo Park, Calif.) and cloned into the previously described pYD317 vector [30]. Cell-free expression reactions were performed with the Xpress CFTM CFPS system essentially as previously described (Yin et al., supra; Zimmerman et al. (2014) Bioconjug. Chem. 25(2): 351-361). For expression of HA1 HA2, and Mfa1 fimbrilin, reactions were performed with IAM pre-treatment, at 25° C., with the addition of oxidized glutathione (2 mM) to create an oxidizing environment for the disulfide bonds. Expression of HA1 and HA2 was performed without IAM treatment of the cell extract; addition of reduced glutathione (8 mM) maintained a reducing expression environment. After 16 h of reaction time, the expressed proteins were isolated from the cell-free reaction mixtures using his-tag affinity purification on Ni Sepharose resin (GE Lifesciences, Pittsburg, Pa.) per the manufacturer's recommendations. Further purification of the HA1 HA2, as well as Mfa1 fimbrilin protein was achieved via cation exchange chromatography on SP ImpRes resin (GE Lifesciences). Briefly, the Ni Sepharose elution pools were exchanged into sodium citrate (50 mM), NaCl (50 mM), pH 4.5, and applied to a column equilibrated in the same buffer. Polished protein was subsequently eluted via gradient elution to Tris (50 mM), NaCl (1 M), pH 7.5. Similarly, HA2 was further purified via anion exchange chromatography on Q ImpRes (GE Lifesciences). Column equilibration and loading was performed in Tris (50 mM), NaCl (50 mM), pH 7.5, with subsequent gradient elution to Tris (50 mM), NaCl (1M), pH 7.5.

After polishing chromatography, all proteins were dialyzed into Dulbecco's PBS and analyzed via SDS-PAGE. and intact mass analysis via Q-TOF (Agilent, Santa Clara, Calif.). In the case of HA1 intact mass analysis conclusively showed that the cysteines were oxidized and had formed the expected disulfide bond.

Cultivation of *P. gingivalis* and Bacterial Purity Assessment:

*Porphyromonas gingivalis* strain A7436 was handled as described previously (Huang et al. (2015) *Mol. Oral. Microbiol.* 30(6):438-450). In brief, freezer stocks were plated on anaerobic blood agar plates, *P. gingivalis* were collected after three days of anaerobic growth at 37° C., harvested organisms were placed into sterile brain-heart infusion broths supplemented with L-cysteine (0.75 g/L), hemin (5 mg/L), and menadione (1 mg/L). After 24 h, bacteria in log-phase growth were harvested by centrifugation and suspended to 1×1010 CFU/mL in 2% carboxymethylcellulose in pyrogen-free saline for oral challenge (100 μL/challenge). For immunizations, broth grown *P. gingivalis* were adjusted to 1×109 CFU/mL in injection-grade saline, and heat-killed (60° C. for 30 min.) prior to injection, and bacterial kill was confirmed by plating. Gram-staining was performed on all *P. gingivalis* broth cultures to ensure purity.

Mice, Immunizations, and Oral Challenge:

Six-week old female BALB/c mice (Charles River Laboratories, Wilmington, Mass.), were randomly separated into six groups (n=8/group), were housed in specific pathogen free facilities, and received water and food ad libitum. All live animal use was performed in accordance with IACUC approvals. Groups included G1) non-immunized/no oral challenge control, G2) non-immunized/*P. gingivalis* oral challenge, G3) heat-killed *P. gingivalis* immunization/*P. gingivalis* oral challenge, G4) Mfa1+HA1+HA2 combined immunization in alum/*P. gingivalis* oral challenge, G5) Mfa1+HA1+HA2 combined immunization in MPL/*P. gingivalis* oral challenge, and G6) Mfa1+HA1+HA2 combined immunization in injection-grade saline/*P. gingivalis* oral challenge. Prior to initiation of immunizations, baseline serum samples were obtained from each animal, and then respective groups of mice were immunized by intramuscular injection of killed *P. gingivalis*, or Mfa1+HA1+HA2 (5 μg of each protein/injection) suspended in either alum (Imject, ThermoFisher Sci, Rockford, Ill.), monophosphoryl lipid A (MPL; Sigma-Aldrich, St. Louis, Mo.), or injection-grade saline. Subsequent intramuscular booster immunizations were delivered 2-, and 4-weeks after the initial immunization. Two-weeks after completion of immunization, a serum sample was obtained from animals immediately prior to oral challenge with *P. gingivalis*. Oral challenge of mice was accomplished as reported previously (Gonzalez et al. (2003) *Infect. Immun.* 71(4):2283-2287). In brief, animals received 10-day oral sulphamethoxazole/trimethoprim (Hi-Tech Pharmical, Amityville, N.Y.) in drinking water, followed by removal of antibiotics and a three-day rest. A *P. gingivalis* slurry (1×1010 CFU/ml+2% carboxymethylcellulose in injection-grade saline) was gently applied to the gums of challenged mice using a syringe fitted with a feeding needle 3-times over a 1-week period. Control animals included those that were mock challenged with 2% carboxymethylcellulose alone. After a 42-day rest following completion of oral challenge, animals were sacrificed, terminal bleeds were obtained, and the head of each mouse was processed for oral bone loss measurements. A final serum sample was collected from each animal at sacrifice, and all serum samples collected were stored at −80° C.

Detection of Mfa1-, HA1-, and HA2-Specific IgG in Mouse Sera:

Antigens (0.5 µg/mL) were plated at 4° C. overnight on Maxisorp plates (NUNC, Rochester, N.Y.), washed three times with PBS containing Tween-20 (0.05%), and blocked with PBS with 1% BSA for a minimum of 1 h. Serial 2-fold diluted serum samples from vaccinated mice (100 µL/well) were added to individual wells and incubated for 2 h at room temperature. Plates were washed, incubated with appropriate isotype specific antibody conjugated to horseradish peroxidase (1:6000 dilution; Southern Biotech, Birmingham, Ala.), visualized with the addition of 100 µL of TMB substrate (Pierce, Rockford, Ill.) for 20-30 min, and reaction stopped by the addition of 50 µL H2SO4 (1.0 M). Absorbance in each well was measured at 450 nm minus the absorbance at 570 nm to correct for plate abnormalities. The resulting data for each sample were plotted to obtain a curve of the reciprocal dilution versus the A450-A570 measurement. The antibody titer was determined as the midpoint of the dilution curve as defined by EC50 calculations using Prism statistical analysis software (GraphPad Software, La Jolla, Calif.). The mean of the EC50 for each cohort was determined to be the final antibody titer.

Measurement of Oral Bone Loss:

Oral bone levels were determined by morphometric analyses, as done previously (Gibson et al. (2001) *Infect. Immun.* 69(12): 7959-7963). After sacrifice, soft tissue was removed around the maxillary molars, and following extensive cleaning, the skulls were stained with methylene blue. Prior to initiation of bone measurements, samples were blinded by a researcher not aware of the groupings. Oral bone measurements at the maxillary molars were obtained using a digital camera affixed to a stereomicroscope from the alveolar bone crest (ABC) to the cementum enamel junction (CEJ) at 14 landmark sites (Baker et al. (1994) *Arch. Oral Biol.* 39(12): 1035-1040). Image analysis was performed using ImageJ (Schneider et al. (2012) Nat. Methods 9(7): 671-675) and onscreen pixel lengths were converted to millimeters, and data obtained from each animal in a group were combined to achieve a group level mean length±SEM.

Statistical Analysis:

Data were analyzed with Prism statistical analysis software (GraphPad). Comparison between groups was performed as indicated using unpaired Student T test, or ANOVA with post-test analysis, and $P<0.05$ was considered significant.

Results:

SDS-PAGE: The purified proteins generated by CFPS were denatured and added to wells (3 µg/well), separated on 4-12% Bis-Tris gradient gels, and stained with coomassie blue. Results of the analysis of the proteins generated under reducing conditions are shown in FIG. 1. Lane 1: molecular mass markers. Lane 2: Mfa1. Lane 3: HA1 Lane 4: HA2.

To determine whether the proteins delivered by intramuscular injection elicited protein-specific IgG antibody responses, and to determine whether different adjuvants (alum vs. MPL) influenced the elicited IgG response, sera were collected from groups of mice at the completion of the immunization period, and at sacrifice were tested for levels of Mfa1-, HA1- and HA2-specific IgG by ELISA. Titration curves for each serum sample were converted to $EC_{50}$ values. As anticipated, sera collected from the non-immunized group of mice prior to oral challenge possessed low levels of IgG to Mfa1, HA1 and HA2. Sera collected from mice immunized with killed *P. gingivalis* A7436 elicited a nominal increase in IgG specific to purified Mfa1, and HA2, with HA2>Mfa1. For the groups of mice immunized IM with the combined proteins suspended in alum, MPL, or injection-grade saline revealed that all mice receiving the vaccine combination responded with antigen-specific IgG responses. Post-immunization levels of IgG to Mfa1 was most robust in MPL adjuvant; MPL>alum or saline. For HA1 alum best facilitated molecule-specific IgG with alum>MPL>saline, while for HA2 alum and MPL facilitated antigen-specific IgG responsivity to similar levels and were both greater than that observed with saline.

Comparisons of IgG levels at sacrifice, revealed that the group of non-immunized mice oral challenged with *P. gingivalis* A7436 generated slight elevation in specific IgG to Mfa1 and HA2, but not against HA1 Immunization with heat-killed *P. gingivalis* A7436 revealed a similar low-level increase in comparison to levels of IgG measured immediately prior to oral challenge, independent of adjuvant or saline, with the exception of measured IgG against HA1 from mice immunized with the protein combination in saline.

Figure 2:
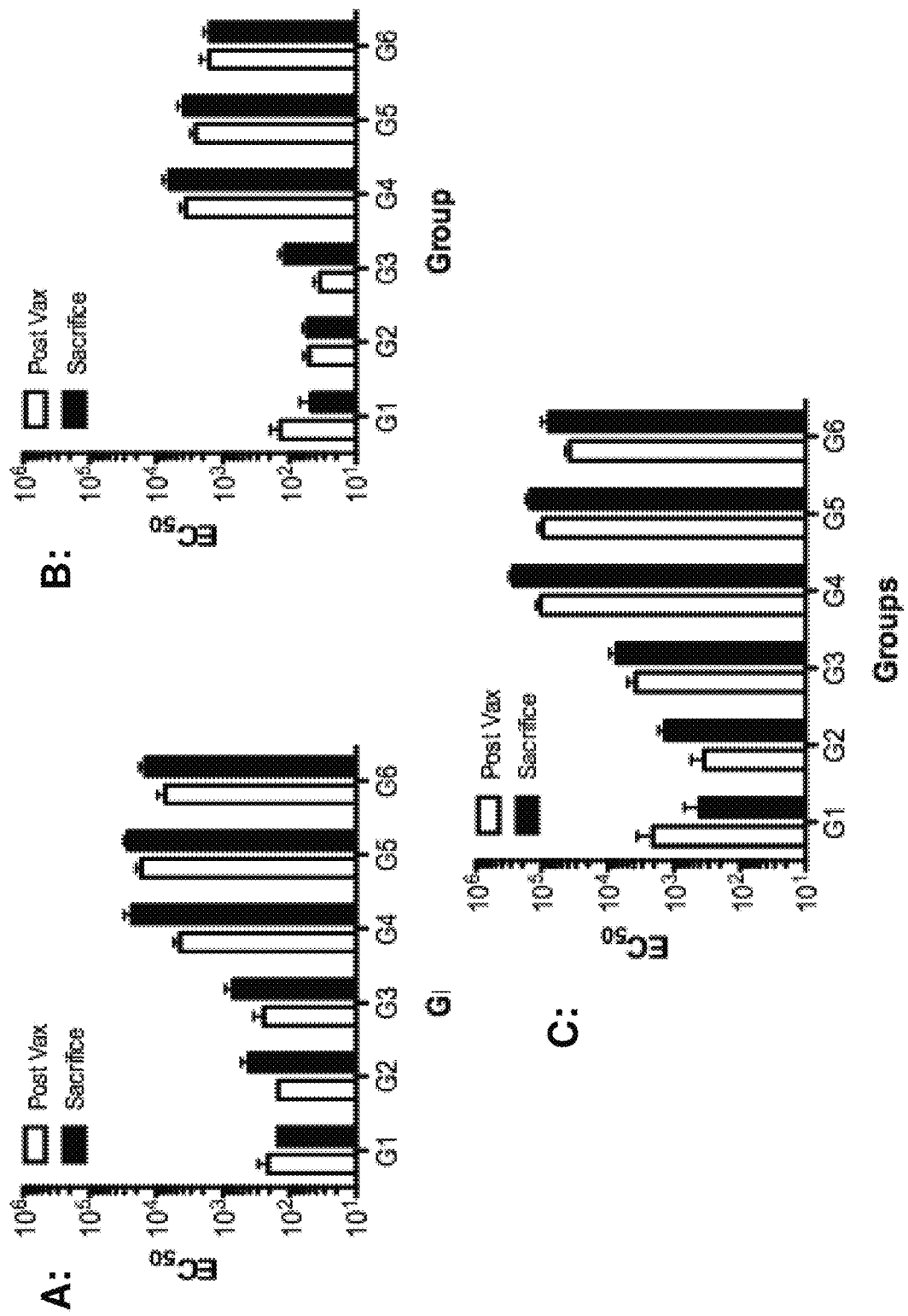
FIG. 2 provides the serum IgG $EC_{50}$ values against *P. gingivalis* Mfa1, HA1 and HA2. Groups of animals G1-G6 served as controls or experimental groups, and serum samples were collected from animals immediately prior to oral challenge (Post-Vax; open bars) or at sacrifice (filled bars), and molecule-specific IgG $EC_{50}$ values were calculated from ELISA data against *P. gingivalis* (A) Mfa1, (B) HA1, and (C) HA2.

FIG. 2 provides the serum IgG $EC_{50}$ values against *P. gingivalis* Mfa1, HA1 and HA2. Groups of animals G1-G6 served as controls or experimental groups, and serum samples were collected from animals immediately prior to oral challenge (Post-Vax; open bars) or at sacrifice (filled bars), and molecule-specific IgG $EC_{50}$ values were calculated from ELISA data against *P. gingivalis* (A) Mfa1, (B) HA1 and (C) HA2.

To understand if the protein combination could effectively limit the extent of *P. gingivalis* elicited oral bone loss, immunized animals were subjected to *P. gingivalis* oral challenge. Groups of mice that were not immunized, or immunized with killed *P. gingivalis* served as controls. In comparison to mock challenged mice (G1), animals orally challenged with *P. gingivalis* A7436 (G2) developed oral bone loss as evidenced by an increase in mean distance from ABC to CEJ (p<0.001). As anticipated, immunization with the killed preparation of *P. gingivalis* A7436 (G3) provided measurable protection from homologous organism-elicited oral bone loss (p<0.01). Groups of mice that received the combination protein vaccine generated from a heterologous strain of *P. gingivalis* suspended in either alum (G4) or MPL (G5) were protected from *P. gingivalis*-elicited oral bone loss (p<0.01 for each vs. *P. gingivalis* oral challenge alone. No differences in the level of protection (ABC to CEJ measurements) was observed between adjuvants, indicating that intramuscular delivery of the vaccine candidate provided similar protective responses (p>0.05). It was also observed that the group of animals immunized with the combination protein vaccine suspended in saline solution (G6) were also protected from *P. gingivalis* oral challenge similar to that observed when the proteins were delivered intramuscular with adjuvant (p>0.05 vs. alum or MPL adjuvants), and the level of protection was similar regardless of adjuvant employed, to that provided by heat-killed whole organism vaccine group (p>0.05 for all).

Figure 3:
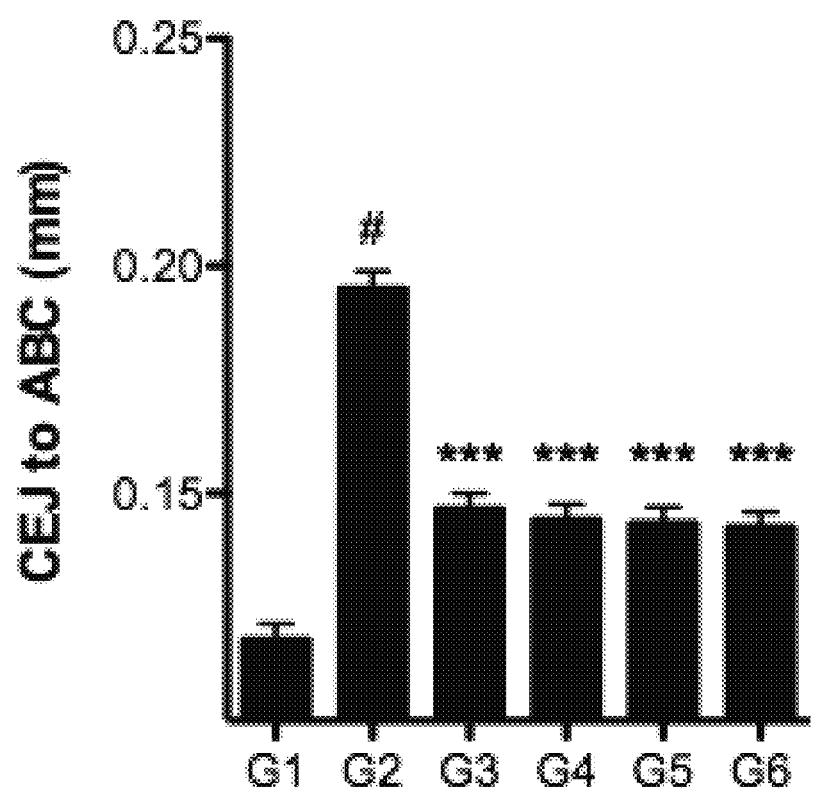
FIG. 3 shows the results of the experiments evaluating the effect of the periodontitis vaccine formulation on oral bone loss in vivo.

FIG. 3 shows the results of the experiments evaluating oral bone loss in vivo. (A) BALB/c mice were randomized into groups (G1-6) and immunized animals received 3 intramuscular injections of combined protein cocktail in respective adjuvant, or in injection-grade saline at 2-week intervals (primary and 2 boosts; red arrows). Immunization control group (G3) received heat-killed *P. gingivalis* (equivalent to $1\times10^7$ CFU/injection). All animals were placed on 10-day sulphamethoxazole/trimethoprim (antibiotics) in drinking water, followed by removal of antibiotics three days prior to mock oral challenge (G1), or *P. gingivalis* oral challenge (3× over a 1-week period; G2-6). After completion of oral challenge (0 wks.), animals were allowed rest for six weeks and then sacrificed. FIG. 3 provides the results, showing the average distance between cementum enamel junction (CEJ) and alveolar bone crest (ABC) in mm±SEM, #=p<0.001 vs. G1 (unchallenged), ***=p<0.01 vs. G2 (*P. gingivalis* oral challenge only) (using ANOVA with Dunns multiple comparisons).

The invention claimed is:

1. An immunogenic composition comprising at least one recombinant polypeptide wherein the at least one recombinant polypeptide comprises:
   (a) an Mfa1 antigen sequence, wherein the Mfa1 antigen sequence comprises a sequence having at least 80% sequence homology to SEQ ID NO: 1 or SEQ ID NO: 4; and
   (b) an HA1 antigen sequence, an HA2 antigen sequence, or both an HA1 antigen sequence and an HA2 antigen sequence, wherein
(i) the HA1 antigen sequence comprises a sequence having at least 80% sequence homology to SEQ ID NO: 2 or SEQ ID NO: 5, and
(ii) the HA2 antigen sequence comprises a sequence having at least 80% sequence homology to SEQ ID NO: 3 or SEQ ID NO: 6.

2. The immunogenic composition according to claim 1, wherein the at least one recombinant polypeptide comprises a first recombinant polypeptide comprising:
   (a) the Mfa1 antigen sequence and the HA1 antigen sequence;
   (b) the Mfa1 antigen sequence and the HA2 antigen sequence; or
   (c) the Mfa1 antigen sequence, the HA1 antigen sequence, and the HA2 antigen sequence.

3. The immunogenic composition according to claim 1, wherein the at least one recombinant polypeptide comprises:
   (a) a first recombinant polypeptide comprising the Mfa1 antigen sequence; and
   (b) a second recombinant polypeptide comprising the HA1 antigen sequence, or the HA2 antigen sequence, or both the HA1 antigen sequence and the HA2 antigen sequence.

4. The immunogenic composition according to claim 1, wherein the at least one recombinant polypeptide comprises:
   (a) a first recombinant polypeptide comprising the Mfa1 antigen sequence;
   (b) a second recombinant polypeptide comprising the HA1 antigen sequence; and
   (c) a third recombinant polypeptide comprising the HA2 antigen sequence.

5. The immunogenic composition of claim 1, wherein the Mfa1 antigen sequence comprises a sequence having at least 80% sequence homology to SEQ ID NO:1, the HA1 antigen sequence comprises a sequence having at least 80% sequence homology SEQ ID NO:2, and the HA2 antigen sequence comprises a sequence having at least 80% sequence homology to SEQ ID NO:3.

6. The immunogenic composition of claim 4, wherein the Mfa1 antigen sequence comprises a sequence having at least 80% sequence homology to SEQ ID NO:1, the HA1 antigen sequence comprises a sequence having at least 80% sequence homology to SEQ ID NO:2, and the HA2 antigen sequence comprises a sequence having at least 80% sequence homology to SEQ ID NO:3.

7. The immunogenic composition of claim 5, wherein the Mfa1 antigen sequence comprises a sequence having at least 90% sequence homology to SEQ ID NO:1, the HA1 antigen sequence comprises a sequence having at least 90% sequence homology to SEQ ID NO:2, and the HA2 antigen sequence comprises a sequence having at least 90% sequence homology to SEQ ID NO:3.

8. The immunogenic composition of claim 1, wherein the Mfa1 antigen sequence comprises a sequence having at least 80% sequence homology to SEQ ID NO:4, the HA1 antigen sequence comprises a sequence having at least 80% sequence homology to SEQ ID NO:5, and the HA2 antigen sequence comprises a sequence having at least 80% sequence homology to SEQ ID NO:6.

9. The immunogenic composition of claim 4, wherein the Mfa1 antigen sequence comprises a sequence having at least 80% sequence homology to SEQ ID NO:4, the HA1 antigen sequence comprises a sequence having at least 80% sequence homology to SEQ ID NO:5, and the HA2 antigen sequence comprises a sequence having at least 80% sequence homology to SEQ ID NO:6.

10. The immunogenic composition of claim 8, wherein the Mfa1 antigen sequence comprises a sequence having at least 90% sequence homology to SEQ ID NO:4, the HA1 antigen sequence comprises a sequence having at least 90% sequence homology to SEQ ID NO:5, and the HA2 antigen sequence comprises a sequence having at least 90% sequence homology to SEQ ID NO:6.

11. A vaccine formulation, comprising the immunogenic composition of claim 1 and at least one excipient.

12. The vaccine formulation of claim 11, wherein the Mfa1 antigen sequence comprises a sequence having at least 80% sequence homology to SEQ ID NO:1, the HA1 antigen sequence comprises a sequence having at least 80% sequence homology to SEQ ID NO:2, and the HA2 antigen sequence comprises a sequence having at least 80% sequence homology to SEQ ID NO:3.

13. The vaccine formulation of claim 12, wherein the Mfa1 antigen sequence comprises a sequence having at least 90% sequence homology to SEQ ID NO:1, the HA1 antigen sequence comprises a sequence having at least 90% sequence homology to SEQ ID NO:2, and the HA2 antigen sequence comprises a sequence having at least 90% sequence homology to SEQ ID NO:3.

14. The vaccine formulation of claim 11, wherein the Mfa1 antigen sequence comprises a sequence having at least 80% sequence homology to SEQ ID NO:4, the HA1 antigen sequence comprises a sequence having at least 80% sequence homology to SEQ ID NO:5, and the HA2 antigen sequence comprises a sequence having at least 80% sequence homology to SEQ ID NO:6.

15. The vaccine formulation of claim 14, wherein the Mfa1 antigen sequence comprises a sequence having at least 90% sequence homology to SEQ ID NO:4, the HA1 antigen sequence comprises a sequence having at least 90% sequence homology to SEQ ID NO:5, and the HA2 antigen sequence comprises a sequence having at least 90% sequence homology to SEQ ID NO:6.

16. The vaccine formulation of claim 11, wherein the at least one excipient is selected from vehicles, solubilizers, emulsifiers, stabilizers, preservatives, isotonicity agents, buffer systems, dispersants, diluents, viscosity modifiers, and absorption enhancers.

17. The vaccine formulation of claim 16, further including an adjuvant.

18. The vaccine formulation of claim 11, formulated as a sterile injectable solution.

19. The vaccine formulation of claim 11, in lyophilized form.

20. A method for immunizing a subject against periodontal disease, comprising administering to the subject an immunologically effective amount of the immunogenic composition of claim 1.

21. A method for immunizing a subject against periodontal disease, comprising administering to the subject an immunologically effective amount of the periodontitis vaccine formulation of claim 11.

22. The method of claim 21, wherein the periodontal disease is associated with a *Porphyromonas* bacterium selected from the group consisting of *P. gingivalis, P. gulae, P. cangingivalis, P. gingivicanis, P. canoris, P. salivosa*, and *P. circumdentaria*.

23. The method of claim 22, wherein the *Porphyromonas* bacterium is *P. gingivalis*.

24. The method of claim 23, wherein the subject is human.

25. The method of claim 22, wherein the *Porphyromonas* bacterium is *P. gulae*.

26. The method of claim 25, wherein the subject is a non-human mammal.

27. The method of claim 21, wherein the vaccine formulation comprises a sterile injectable solution and is administered to the subject by injection.

28. The method of claim 27, wherein the vaccine formulation is administered as an intramuscular injection.

29. The method of claim 27, wherein the vaccine formulation is administered as a gingival injection.

30. The method of claim 21, wherein the vaccine formulation is administered transmucosally.

31. The method of claim 30, wherein the vaccine formulation is administered intranasally.

32. The method of claim 21, wherein the vaccine formulation is administered once.

33. The method of claim 21, wherein the vaccine formulation is administered two or more times.

34. The method of claim 21, wherein the subject exhibits symptoms of periodontitis and the vaccine formulation is administered as a therapeutic vaccine.

35. A method for reducing the risk of periodontitis developing in a subject, the method comprising administering to the subject an immunologically effective amount of the immunogenic composition of claim 1.

36. A method for reducing the risk of periodontitis developing in a subject, the method comprising administering to the subject an immunologically effective amount of the vaccine formulation of claim 11.

37. The method of claim 36, wherein the subject has at least one risk factor of developing periodontitis.

38. The method of claim 37, wherein the at least one risk factor is selected from age, genetic predisposition, a systemic disease, the presence of endodontic lesions or abscesses, or a combination thereof.

39. A method for reducing bone loss caused by periodontal disease, comprising administering to a subject in need of such treatment an immunologically effective amount of the immunogenic composition of claim 1.

40. A method for preventing bone loss caused by periodontal disease, comprising administering to a subject in need of such treatment an immunologically effective amount of the vaccine formulation of claim 11.

41. A method for reducing inflammation caused by periodontal disease, comprising administering to a subject in need of such treatment an effective amount of the immunogenic composition of claim 1.

42. A method for reducing inflammation caused by periodontal disease, comprising administering to a subject in need of such treatment an effective amount of the vaccine formulation of claim 11.

43. The immunogenic composition of claim 1, wherein the at least one recombinant polypeptide is produced by cell-free protein synthesis.

* * * * *

UNITED STATES PATENT AND TRADEMARK OFFICE
CERTIFICATE OF CORRECTION

PATENT NO. : 10,835,590 B2
APPLICATION NO. : 16/158155
DATED : November 17, 2020
INVENTOR(S) : Jeffery C. Fairman Page 1 of 1

It is certified that error appears in the above-identified patent and that said Letters Patent is hereby corrected as shown below:

In the Claims

At Column 33, Claim number 5, Line number 3:
"sequence homology SEQ ID NO:2, and the HA2 antigen"
Should read:
-- sequence homology to SEQ ID NO:2, and the HA2 antigen --

At Column 34, Claim number 21, Line number 22:
"immunologically effective amount of the periodontitis vac-"
Should read:
-- immunologically effective amount of the vaccine --

Signed and Sealed this
Twenty-third Day of February, 2021

Drew Hirshfeld
*Performing the Functions and Duties of the*
*Under Secretary of Commerce for Intellectual Property and*
*Director of the United States Patent and Trademark Office*